United States Patent
Fladby et al.

(10) Patent No.: US 11,988,677 B2
(45) Date of Patent: *May 21, 2024

(54) METHODS AND COMPOSITIONS FOR MONITORING PHAGOCYTIC ACTIVITY

(71) Applicant: INVEN2 AS, Oslo (NO)

(72) Inventors: Tormod Fladby, Blommenholm (NO); Lisbeth Johnsen, Finstadjordet (NO); Hanne Mali Mollergard, Rasta (NO)

(73) Assignee: INVEN2 AS, Oslo (NO)

( * ) Notice: Subject to any disclaimer, the term of this patent is extended or adjusted under 35 U.S.C. 154(b) by 168 days.

This patent is subject to a terminal disclaimer.

(21) Appl. No.: 17/582,355

(22) Filed: Jan. 24, 2022

(65) Prior Publication Data

US 2022/0341948 A1    Oct. 27, 2022

Related U.S. Application Data

(63) Continuation of application No. 13/989,950, filed as application No. PCT/IB2011/002999 on Nov. 28, 2011, now Pat. No. 11,231,426.

(60) Provisional application No. 61/417,559, filed on Nov. 29, 2010.

(51) Int. Cl.
*G01N 33/68* (2006.01)
*C07K 14/47* (2006.01)
*C07K 16/18* (2006.01)

(52) U.S. Cl.
CPC ...... *G01N 33/6896* (2013.01); *C07K 14/4711* (2013.01); *C07K 16/18* (2013.01); *C07K 2317/34* (2013.01); *G01N 2800/2814* (2013.01); *G01N 2800/2821* (2013.01)

(58) Field of Classification Search
CPC ....... G01N 33/6896; G01N 2800/2814; G01N 2800/2821; C07K 14/4711; C07K 16/18; C07K 2317/34
See application file for complete search history.

(56) References Cited

U.S. PATENT DOCUMENTS

| | | | |
|---|---|---|---|
| 6,022,859 A | 2/2000 | Kiessing et al. | |
| 6,750,324 B1 | 6/2004 | Schenk et al. | |
| 11,231,426 B2 * | 1/2022 | Fladby | C07K 16/18 |

FOREIGN PATENT DOCUMENTS

| WO | WO 1997/37228 | 10/1997 |
|---|---|---|
| WO | WO 2000/72880 | 12/2000 |
| WO | WO 2003/070760 | 8/2003 |
| WO | WO 2005/058940 | 6/2005 |
| WO | WO 2010/011947 | 1/2010 |

OTHER PUBLICATIONS

Wilcock, DM et. al. "Passive Amyloid Immunotherapy Clears Amyloid and Transiently Activates Microglia in a Transgenic Mouse Model of Amyloid Deposition", 2004, The Journal of Neuroscience, 24(27), 6144-6151. (Year: 2004).*
Seubert, P et. al. "Isolation and quantification of soluble Alzheimer's β-peptide from biological fluids", 1992, Nature, 359, 325-327. (Year: 1992).*
"Treatment of Severe Alzheimer's Disease: Evaluation of Efficacy and Safety of Galantamine Hydrobromide in a Controlled Study", 2009, ClinicalTrials.gov, Version 19. (Year: 2009).*
International Search Report and Written Opinion dated Aug. 27, 2012, PCT/IB2011/002999.
Boland et al.(2010), "Macroautophagy Is Not Directly Involved in the Metabolism of Amyloid Precursor Protein," The Journal of Biological Chemistry, vol. 285, No. 48, pp. 37415-37426.
Braak et al (1991), "Nuropathological Stageing of Alzheimer-Related Changes," Acta Neuropathol. 82:239-259.
Fiala et al. (2005), "Ineffective phagocytosis of amyloid-b by macrophages of Alzheimer's disease patients," J. Alzheimers Dis. 7:221-232.
Hebert et al. (2003), Alzheimer Disease in the US Population, Arch. Neurol. 60(8):1119-22.
Lorenzen et al. (2010), "Rapid and Direct Transport of Cell Surface APP to the Lysosome defines a novel selective pathway," Mol. Brain 3:11.
Malito et al. (2008), "Amyloid B-degrading cryptidases: insulin degrading enzyme, neprilysin, and presequence peptidase," Cell Mol Life Sci, 65(16):2574-2585.
Oi, et al. (1986), "Chimeric Antibodies," BioTechniques 4(3):214.
Schenk et al (1999), "Immunization with amyloid-B attenuates Alzheimer-disease-like pathology in the PDAPP mouse," Nature 400:173-177.
Simard et al. (2006), "Bone Marrow-Derived Microglia Play a Critical Role in Restricting Senile Plaque Formation in Alzheimer's Disease," Neuron 49:489-502.
Spira et al. (1984), "The Identification of Monoclonal Class Switch Variants by Sib Selection and an ELISA Assay," J. Immunol. Methods 74:307-315.
Steplewski et al. (1985), "Isolation and characterization of anti-monosialoganglioside monoclonal antibody 19-9 class-switch variants," Proc. Natl. Acad. Sci. 82:8653-8657.

(Continued)

*Primary Examiner* — Nelson B Moseley, II
*Assistant Examiner* — Alyssa Rae Stonebraker
(74) *Attorney, Agent, or Firm* — Casimir Jones, S.C.; J. Mitchell Jones

(57) ABSTRACT

The invention relates to compositions and methods for monitoring phagocytic activity (e.g., diseases and conditions relating to phagocytic activity). In particular, the invention relates to compositions and methods for diagnosing, monitoring, and/or assessing risk of neurodegenerative diseases (e.g., AD).

8 Claims, 11 Drawing Sheets

Specification includes a Sequence Listing.

(56) References Cited

OTHER PUBLICATIONS

Vellas et al. (2007), "Disease-modifying trials in Alzheimer's disease: a European task force consensus," Lancet Neurol. 6:56-62.
Fallitto et al., Recognition sequence design for peptidyl modulators of beta-amylod aggregation and toxicity, Biochemisty. 38(12):3570-3578, 1999.
Akiyama et al.. Neuroscience Letters, 206:169-172, 1996.
Nlajumdar et al.. Neurobiology of Aging, 29(5): 707-715. May 2008.
Nlichaud et al.. Cell Reports. 5:646-653, Nov. 2013.
Cirrito et al., J Clin Invest. 115(11):3285-3290. Nov. 2005.
Bateman et al., Nature Medicine, 12(7): 856-861. Jul. 2006.
Fagan et al.. Ann Neurol., 59(3):512-519. 2006.
Maddalena et al., Neurodegenerative Diseases, 1:231-235. 2004.
Nlajumdar et al.. Neurobiol Aging, 29(5): 707-715. May 2008.
Roher et al., Alzheimer's & Dementia, 5:18-29, 2009.
Chen et al., Biochemical and Biophysical Res Comm, 213(1):96-103, (Year: Aug. 1995).
Meda et al., J Immunol 157:1213-1218 (Year: 1996).
Condic et al., Brain, Behavior, and Immunity 41 (2014) 116-125 (Year: 2014).

\* cited by examiner

Typical result from an *in vitro* phagocytosis-assay: Dose-response curve, and microscopy showing Aβ fagocytosis Detection and quantification of Alzheimer specific APP metabolites using real time PCR

METHODS AND COMPOSITIONS FOR MONITORING PHAGOCYTIC ACTIVITY

CROSS-REFERENCE TO RELATED APPLICATIONS

This application is a continuation of U.S. patent application Ser. No. 13/989,950, filed Jun. 10, 2013, now allowed as U.S. Pat. No. 11,231,426, which is a 371 U.S. National Entry of International Patent Application No. PCT/IB2011/002999, filed Nov. 28, 2011, which claims priority to U.S. Provisional Patent Application No. 61/417,559, filed Nov. 29, 2010, the contents of which are hereby incorporated by reference in their entireties.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 2,000 Byte ASCII (Text) file named "31699-303_ST25" created on Jan. 24, 2022.

FIELD OF THE INVENTION

The invention relates to compositions and methods for monitoring phagocytic activity (e.g., diseases and conditions relating to phagocytic activity). In particular, the invention relates to compositions and methods for diagnosing, monitoring, and/or assessing risk of neurodegenerative diseases (e.g., Alzheimer's disease (AD)).

BACKGROUND OF THE INVENTION

AD, the most common cause of dementia, is an acquired cognitive and behavioral impairment that interferes with social and occupational functioning. AD is a major public health problem from the economic perspective, causing not only tremendous economic burden relating to patients themselves, but also due to social, economic, physical, and psychological impacts on caregivers. In the United States, the cost of caring for patients with dementia was $144 billion per year in 2009, and the average yearly cost for healthcare and long-term care services per patient was about $33,007 in 2004, the most recent data available (Alzheimer's Association (2010) Alzheimer's & Dementia 6:158-194).

AD affects approximately 5.3 million people in the United States as of 2010 (Alzheimer's Association (2010) Alzheimer's & Dementia 6:158-194) and 26.6 million individuals worldwide as of 2006. A larger number of individuals have decreased levels of cognitive function (e.g., measurable mild cognitive impairment (MCI) or even earlier only subjective cognitive impairment (SCI)) that frequently evolve into a full-blown dementia, thereby increasing the number of affected persons. By 2030, an estimated 7.7 million Americans aged 65 and older will have AD (Hebert et al. (2003) Arch. Neurol. 60(8):1119-22). Statistical projections indicate that the number of persons affected by the disorder in the United States could range from 11-16 million by the year 2050 (Hebert et al. (2003) Arch. Neurol. 60(8):1119-22).

The causative factors of sporadic AD remain elusive, but disease progression is correlated with hallmark anatomic pathological signs including neurofibrillary tangles (NFTs); senile plaques (SPs) at the microscopic level; and cerebrocortical atrophy. Amyloid deposition is also implicated in two other common causes of dementia, vascular dementia (VaD) and dementia with Lewy bodies (DLB), as well as inclusion body myositis, a muscle disease. Although AD follows a typical course of progression, there is a dearth of definitive diagnostic methods, particularly for early-stage AD. This is particularly problematic since MCI and early-stage AD are clinically valuable periods for implementation of disease-modifying therapies (Vellas et al. (2007) Lancet Neurol. 6:56-62). This is significant because the widespread damage caused by AD is most likely irreversible at later stages of disease progression (Braak et al. (1991) ActaNeuropathol. 82:239-259).

Improved methods and compositions are needed for detection, diagnosis, and monitoring of neurodegenerative diseases, e.g., AD.

SUMMARY OF THE INVENTION

The invention relates to compositions and methods for monitoring phagocytic activity (e.g., diseases and conditions relating to phagocytic activity). In particular, the invention relates to compositions and methods for detecting, diagnosing, monitoring, and/or assessing risk of neurodegenerative diseases (e.g., AD).

Numerous diseases and conditions involve activation of macrophages and proteolysis of proteins, e.g., pathologic aggregates of endogenous proteins. For example, in AD, the formation of amyloid plaques in the brain occurs when aggregates of amyloid beta (Aβ) peptides are formed following proteolysis of amyloid precursor protein (APP). Immunization of an individual with Aβ peptides triggers phagocytosis (Schenk et al. (1999) Nature 400:173-177; herein incorporated by reference in its entirety). Immune activity may also be involved in the natural evolution of amyloid pathology, e.g., the continuous level of phagocytic activity may contribute to plaque load over time. There is evidence that macrophages circulate from the bone marrow to the central nervous system in pathological conditions and contribute to plaque clearing in mouse models of AD (Simard et al. (2006) Neuron 49:489-502; herein incorporated by reference in its entirety), and macrophages isolated from AD patients exhibit reduced phagocytosis of Aβ peptides compared to macrophages from non-AD patients (Fiala et al. (2005) J. Alzheimers Dis. 7:221-232; herein incorporated by reference in its entirety). Experiments conducted during the course of developing some embodiments of the present invention identified Aβ peptides present in activated macrophages isolated from peripheral blood samples (e.g., SEQ ID NOs. 1-5). The peptides range from 6 to 11 amino acids in length. Accordingly, in some embodiments, determination of the level, presence, or absence of Aβ peptides (e.g., SEQ ID NOs.:1-5) in leukocytes or macrophages (e.g., activated macrophages) of a patient finds use as method for diagnosing, monitoring, and/or assessing the risk of disease (e.g., AD, vascular dementia, dementia with Lewy bodies, inclusion body myositis).

In some embodiments, methods of the present invention comprise obtaining a sample from a subject (e.g., a human subject), without limitation to the sample type. In preferred embodiments, the sample comprises leucocytes and/or macrophages (e.g., activated macrophages). The sample may comprise blood (e.g., peripheral blood), cerebrospinal fluid (CSF), tissue (e.g., lung, spleen, liver, brain, pancreas, small intestine, tumour). In some embodiments, the sample is a bronchial alveolar lavage (BAL) sample. In some embodiments, the sample is bone marrow. In particularly preferred embodiments, the sample is a blood sample or a CSF sample.

In some embodiments, methods of the present invention comprise a step of isolating or enriching for macrophages (e.g., activated macrophages), without limitation to the technique used for such isolation or enrichment (e.g., as described in *Macrophages* (2000) ed. Paulnock, D. M., Oxford Univ. Press, Oxford, UK). Examples of macrophage isolation or purification techniques include but are not limited to adhesion or adherence methods (e.g., adherence to solid support (e.g., plastic, glass) whether such support is coated (e.g., coated with gelatine, microexudate, collagen, lysine) or uncoated), differential centrifugation (e.g., gradient centrifugation, isopycnic gradient centrifugation, Ficoll-Hypaque gradient centrifugation, Percoll gradient centrifugation), flow cytometry, fluorescent activated cell sorting (FACS), flotation techniques, antibody-mediated affinity techniques (e.g., immunoprecipitation, antibody-mediated binding to solid support (e.g., magnetic beads, non-magnetic particles, plates, wells, cards, chips, slides, arrays, etc.). In some embodiments, the macrophage (e.g., activated macrophage) purification or isolation technique involves binding of macrophages with a binding partner (e.g., antibody) that is non-covalently or covalently associated with a moiety used for direct or indirect detection (e.g., a fluorescent tag, biotin, streptavidin, a radioisotope, an epitope, an affinity tag).

In some embodiments, methods of the present invention comprise detection of the level of one or more biomarkers of a condition or disease state (e.g., AD) present in leucocytes and/or macrophages (e.g., activated macrophages), without limitation to the technique used for such detection. In preferred embodiments, one or more of the biomarkers are Aβ peptides (e.g., SEQ ID.NOs.:1-5). In some embodiments, the level of one or more biomarkers (e.g., Aβ peptides, SEQ ID.NOs.:1-5) is determined quantitatively. In some embodiments, the presence or absence of one or more biomarkers is determined qualitatively. In some embodiments, a decrease in the level(s) of one or more biomarkers (e.g., in a sample of tissue or biological fluid, in a sample enriched for leucocytes and/or macrophages (e.g., activated macrophages)) relative to a control is correlated with an increased risk of disease (e.g., AD), diagnosis of disease (e.g., AD). In some embodiments, samples comprising macrophages and/or microglia are assessed for level of phagocytic activity, e.g., are exposed to a first polypeptide (e.g., an Aβ peptide, APP) for a period of time and the level of phagocytosis of the polypeptide is determined. In some embodiments, the presence, absence, or level of polypeptides smaller in length than the first polypeptide (e.g., a second Aβ peptide, SEQ ID NOs:1-5) serves as an indication of the level of phagocytic and/or proteolytic activity in the original sample.

In some embodiments, methods of the present invention involve comparing the level of one or more biomarkers (e.g., Aβ peptides, SEQ ID.NOs.:1-5) in samples from the same patient at one or more different time points (e.g., longitudinal sampling), e.g., where such levels are correlated with disease progression. In some embodiments, methods of the present invention involve comparing the level of one or more biomarkers (e.g., Aβ peptides, SEQ ID.NOs.:1-5) in a sample from a patient relative to the level(s) found in a sample from a control subject lacking disease (e.g., AD). In some embodiments, methods of the present invention involve comparing the level of one or more biomarkers (e.g., Aβ peptides, SEQ ID.NOs.:1-5) in a sample from a first subject relative to the average, mean, or other statistically determined level(s) (e.g., "standard level(s)") found in samples from a plurality of control subject slacking disease (e.g., AD), wherein the level of the one or more biomarker(s) in the first subject is abnormal if there is a statistically significant difference from the standard level.

In some embodiments, the prevent invention relates to compositions comprising isolated Aβ peptides with greater than 80%, greater than 85%, greater than 90%, preferably greater than 95%, most preferably greater than 99% identity to SEQ ID.NOs.:1-5, and agent(s) used for their specific detection (e.g., antibodies capable of specific detection of Aβ peptides with greater than 80%, greater than 85%, greater than 90%, preferably greater than 95%, most preferably greater than 99% identity to SEQ ID.NOs.:1-5). In some embodiments, the present invention relates to kits comprising isolated Aβ peptides with greater than 80%, greater than 85%, greater than 90%, preferably greater than 95%, most preferably greater than 99% identity to SEQ ID.NOs.:1-5 and/or agent(s) used for their specific detection (e.g., antibodies capable of specific detection of Aβ peptides with greater than 80%, greater than 85%, greater than 90%, preferably greater than 95%, most preferably greater than 99% identity to SEQ ID.NOs.:1-5).

In certain embodiments, the present invention provides a composition comprising an isolated peptide, the isolated peptide being 6 to 11 amino acids in length, the peptide having at least 80% identity to an amino acid sequence such as SEQ ID NO:1, SEQ ID NO:2, SEQ ID NO:3, SEQ ID NO:4, or SEQ ID NO:5. In some embodiments, the peptide has at least 85% identity to an amino acid sequence such as SEQ ID NO:1, SEQ ID NO:2, SEQ ID NO:3, SEQ ID NO:4, or SEQ ID NO:5. In some embodiments, the peptide has at least 90% identity to an amino acid sequence such as SEQ ID NO:1, SEQ ID NO:2, SEQ ID NO:3, SEQ ID NO:4, or SEQ ID NO:5. In some embodiments, the peptide has at least 95% identity to an amino acid sequence such as SEQ ID NO:1, SEQ ID NO:2, SEQ ID NO:3, SEQ ID NO:4, or SEQ ID NO:5. In some embodiments, the peptide has at least 99% identity to an amino acid sequence such as SEQ ID NO:1, SEQ ID NO:2, SEQ ID NO:3, SEQ ID NO:4, or SEQ ID NO:5.

In certain embodiments, the present invention provides a kit for the detection, diagnosis, and/or monitoring of a disease, the kit comprising components such as one or more synthetic peptides having at least 80% identity to an amino acid sequence such as SEQ ID NO:1, SEQ ID NO:2, SEQ ID NO:3, SEQ ID NO:4, or SEQ ID NO:5 and one or more first binding reagents specifically capable of binding to a peptide having at least 80% identity to an amino acid sequence such as SEQ ID NO:1, SEQ ID NO:2, SEQ ID NO:3, SEQ ID NO:4 or and SEQ ID NO:5. In some embodiments, the disease is a type such as AD, vascular dementia, or dementia with Lewy bodies. In some embodiments, the binding reagent is an antibody. In some embodiments, the kit further comprises components such as synthetic Aβ$_{42}$, media, a macrophage-specific binding reagent, or a secondary binding reagent capable of the one or more first binding reagents.

In certain embodiments, the present invention provides a method for diagnosing, monitoring, and/or assessing the risk of a neurodegenerative disease in a subject, the method comprising 1) obtaining a sample from a subject, the sample comprising a cell type such as leucocytes, monocytes, macrophages, or activated macrophages, and b) detecting the level of a peptide in the sample, wherein the peptide has at least 80% identity to an amino acid sequence such as SEQ ID NO:1, SEQ ID NO:2, SEQ ID NO:3, SEQ ID NO:4, or SEQ ID NO:5, wherein an abnormal level of the peptide relative to a standard level is indicative of the presence or severity of the neurodegenerative disease in the subject. In some embodiments, the neurodegenerative disease is a type such as AD, vascular dementia, and dementia with Lewy bodies. In some embodiments, the sample is a type such as a blood sample, a tissue sample, or a cerebrospinal fluid sample. In some embodiments, the cell type is macrophage. In some embodiments, the cell type is activated macrophage. In some embodiments, the standard level a type such as the level in the subject at a different time point, the level in a different subject lacking the neurodegenerative disease, and the average level in a plurality of subjects lacking the neurodegenerative disease. In some embodiments the method further comprises isolating the cell type such asleucocytes, monocytes, macrophages, or activated macrophages. In some embodiments, the isolated cells are macrophages. In some embodiments, the method further comprises incubating the isolated cells with synthetic Aβpolypeptide. In some embodiments, the synthetic Aβpolypeptide is $A\beta_{42}$.

Additional embodiments will be apparent to persons skilled in the relevant art based on the teachings contained herein.

DEFINITIONS

Figure 1:
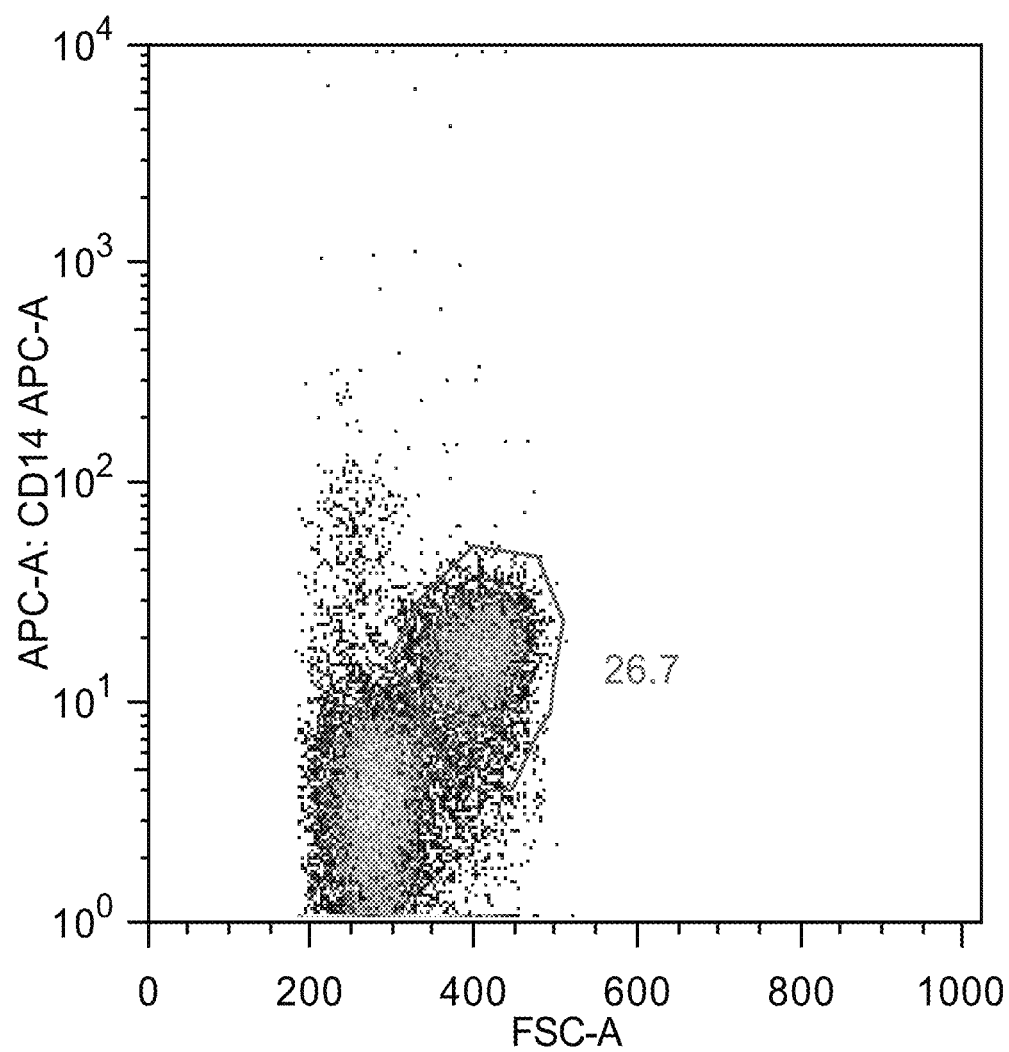
FIG. 1 provides a depiction of Aβ content in monocytes.

To facilitate an understanding of the present invention, a number of terms and phrases are defined below:

As used herein, the term "sensitivity" is defined as a statistical measure of performance of an assay (e.g., method, test), calculated by dividing the number of true positives by the sum of the true positives and the false negatives.

As used herein, the term "specificity" is defined as a statistical measure of performance of an assay (e.g., method, test), calculated by dividing the number of true negatives by the sum of true negatives and false positives.

As used herein, the term "informative" or "informativeness" refers to a quality of a marker or panel of markers, and specifically to the likelihood of finding a marker (or panel of markers) in a positive sample.

As used herein, "an individual is suspected of being susceptible at risk for AD" is meant to refer to an individual who is at an above-average risk of developing AD (AD). Examples of individuals at a particular risk of developing AD are those whose family medical history indicates above average incidence of AD, individuals of advanced age, individuals exhibiting signs or symptoms of MCI or SCI. Other factors which may contribute to an above-average risk of developing AD may be based upon an individual's specific genetic, medical, psychological, psychosocial, and/or behavioral background and characteristics.

As used herein, the term "isolated" when used in relation to material (e.g., a cell, a leukocyte, a macrophage, an activated macrophage, a microglia) refers to a material that is identified and separated from at least one component or contaminant with which it is ordinarily associated in its natural source. An isolated material is such present in a form or setting that is different from that in which it is found in nature.

As used herein, the terms "immunoglobulin" and "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

As used herein, the term "antigen binding protein" refers to proteins that bind to a specific antigen. "Antigen binding proteins" include, but are not limited to, immunoglobulins, including polyclonal, monoclonal, chimeric, and humanized antibodies; Fab fragments, F(ab')$_2$ fragments, and Fab expression libraries; and single chain antibodies.

The term "epitope" as used herein refers to that portion of an antigen that makes contact with a particular immunoglobulin.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "subject" refers to any animal (e.g., a mammal), including, but not limited to, humans, non-human primates, rodents, and the like (e.g., that is to be the recipient of a particular treatment (e.g., transplant graft) or that is a donor of a graft. The terms "subject" and "patient" are used interchangeably in reference to a human subject, unless indicated otherwise herein (e.g., wherein a subject is a graft donor).

As used herein, the term "sample" is used in its broadest sense. For example, in some embodiments, it is meant to include a specimen (e.g., blood sample, cerebrospinal fluid (CSF) sample). In preferred embodiments, it is meant to include a biological sample.

The present invention is not limited by the type of biological sample used or analyzed. The present invention is useful with a variety of biological samples including, but are not limited to, tissue (e.g., organ (e.g., heart, liver, brain, lung, stomach, intestine, spleen, kidney, pancreas, and reproductive (e.g., ovaries) organs; lung biopsy), glandular, skin, and muscle tissue), cell (e.g., blood cell (e.g., lymphocyte or erythrocyte), muscle cell, tumor cell, bronchial cell, bronchioalveolar cells, and skin cell), gas, bodily fluid (e.g., tracheal aspirate fluid, bronchoalveolar fluid, bronchoalveolar lavage sample, blood or portion thereof, serum, plasma, urine, semen, saliva, etc), or solid (e.g., stool) samples obtained from a human (e.g., adult, infant, or embryo) or animal (e.g., cattle, poultry, mouse, rat, dog, pig, cat, horse, and the like). Biological samples may be obtained from all of the various families of domestic animals, as well as feral or wild animals, including, but not limited to, such animals as ungulates, bear, fish, lagamorphs, rodents, etc.

Biological samples also include biopsies and tissue sections (e.g., biopsy or section of tumor, growth, rash, infection, or paraffin-embedded sections), medical or hospital samples (e.g., including, but not limited to, bronchoalveolar lavage fluid (BAL) samples, tracheal aspirate fluid, blood samples, saliva, buccal swab, cerebrospinal fluid, pleural fluid, milk, colostrum, lymph, sputum, vomitus, bile, semen, oocytes, cervical cells, amniotic fluid, urine, stool, hair and sweat), and laboratory samples (e.g., subcellular fractions).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample. In yet a further example, a specific cell type (e.g., leukocyte, macrophage, activated macrophage, microglial cell) may be purified or enriched for using a cell sorting technique (e.g., flow cytometery, fluorescence-activated cell sorting (FACS)).

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

DETAILED DESCRIPTION OF THE INVENTION

The present invention provides compositions, methods and kits relating to the detection, monitoring, diagnosis, or assessment of risk of developing a neurodegenerative disease (e.g., AD, vascular dementia, dementia with Lewy bodies, inclusion body myositis, or other neurodegenerative disease). In some embodiments, the present invention finds use in characterizing alterations in phagocytic activity of macrophages (e.g., phagocytosis of pathological polypeptides, e.g., phagocytosis of Aβ-peptides, phagocytosis of amyloid precursor protein). In some embodiments, the invention comprises methods for diagnosing monocyte/macrophage phagocytic activity in samples from body fluids, e.g., by detection of the level, presence, or absence of phagocytosed peptide fragments (e.g., Aβ-peptides, SEQ ID NOs:1-5).

Figure 2:
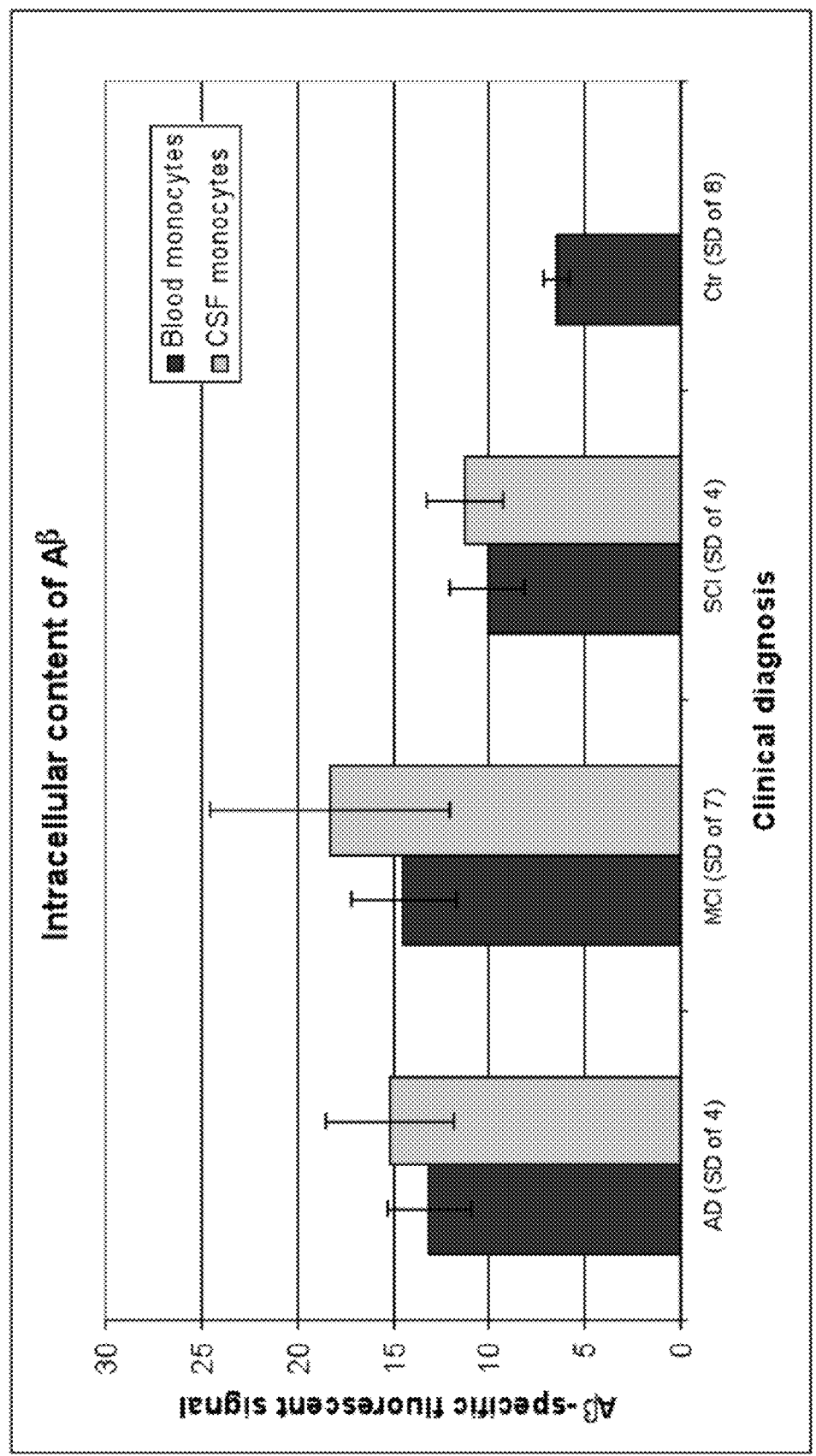
FIG. 2 provides data associating intracellular content of Aβ with clinical diagnosis.
Figure 3:
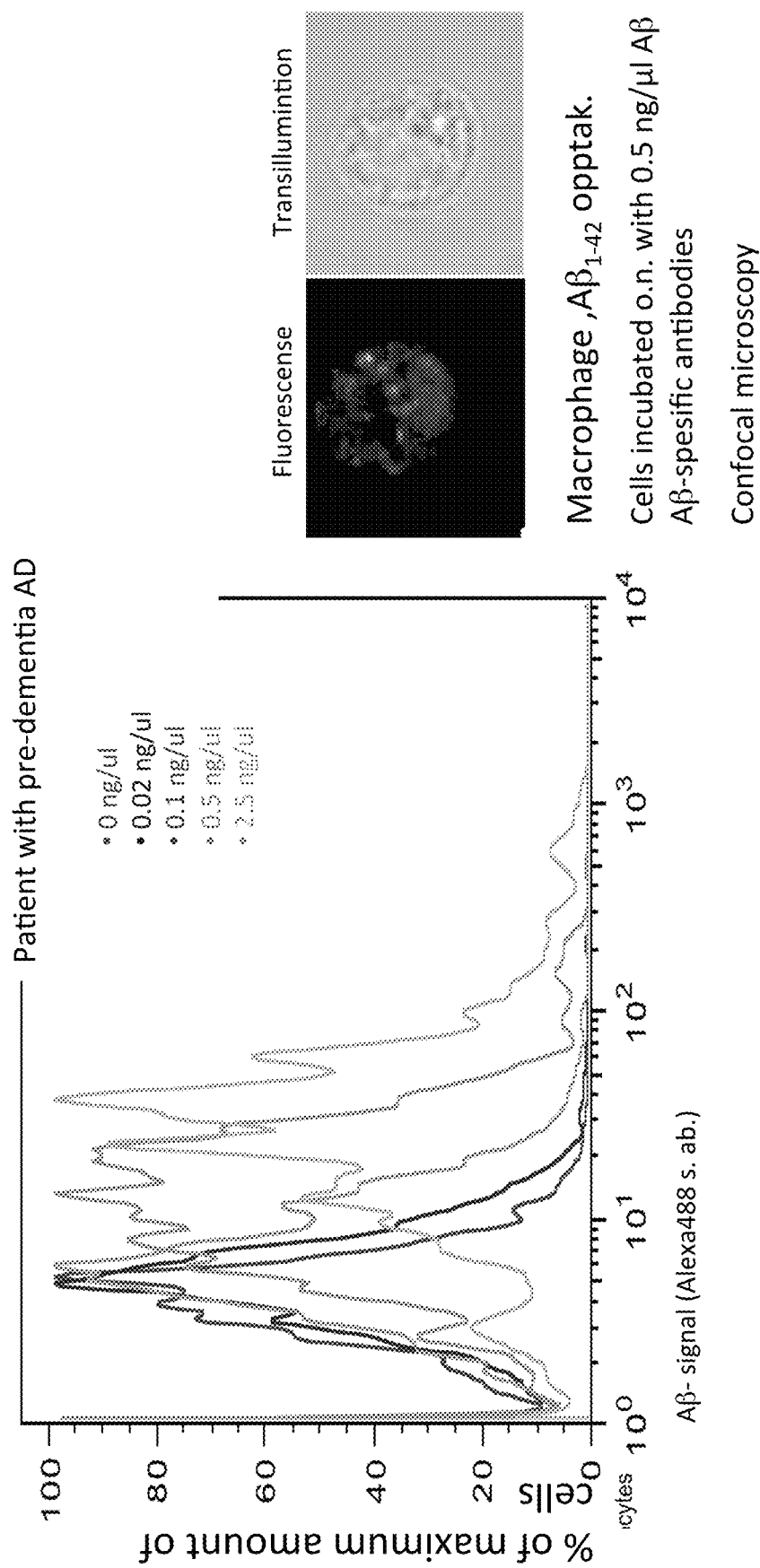
FIG. 3 provides a dose response curve typical for an in vitro phagocytosis assay shows confocal microscopy of a macrophage incubated with 0.5 ng/μL $A\beta_{1-42}$ overnight and labelled with green fluorescing $A\beta_{1-42}$-specific antibodies (6E10 and 4G8). Left, fluorescent signal observed during immunoconfocal microscopy. Right, transillumination.

In experiments conducted during the course of developing some embodiments of the present invention, it was shown that blood-derived monocytes/macrophages internalize Aβ$_{1-42}$ in an in vitro setting. A depiction of Aβ content is provided in FIG. 1. FIG. 2 provides data associating intracellular content of Aβ with clinical diagnosis. FIG. 3 provides a dose response curve typical for an in vitro phagocytosis assay and shows that the internalization occurs via the endosomal-lysosomal system as the $A\beta_{1-42}$-specific green fluorescence appears in intracellular granula; see also (Boland et al. (2010), in press, doi: 10.1074/jbc.M110.186411; Lorenzen et al. (2010) Mol. Brain 3:11; each herein incorporated by reference in its entirety). It is postulated that method of evaluating the efficiency of said clearance is needed to improve the diagnostic process, e.g., when diagnosing AD.

In some embodiments, the present invention provides methods for diagnosing monocyte/macrophage phagocytic activity in samples, e.g. body fluid samples, by detection of phagocytosed peptide-fragments. Experiments conducted during the course of developing some embodiments of the present invention allowed identification of peptide fragment structures specific for phagocytosed and partially degraded amyloid precursorprotein (APP), e.g., as described in Example 1 (e.g., SEQ ID NOs.:1-5). In some embodiments, the peptides are from about 5 to about 9, 10, 11, 12, 13, 14, 15, 16, 17, 18, 19, or 20 amino acids in length, with the proviso that a portion of the peptide is at least 80%, 90%, or 100% identical to one of SEQ ID NOs:1-5. In some embodiments, the portion of the peptide that is at least 80%, 90%, or 100% identical to one of SEQ ID NOs:1-5 is flanked by N or C-terminal amino acid segments. In some embodiments, Aβ peptide fragments (e.g., SEQ ID NOs:1-5) are synthesized (e.g., chemically synthesized, synthesized by recombinant expression), and animals are immunized with individual peptides (e.g., peptides encoded by SEQ ID NOs:1-5) in order to produce peptide-specific antibodies. In some embodiments, such peptide-specific antibodies may be used in a kit (e.g., a kit for the diagnosis, monitoring, or determining the risk of developing) for a disease (e.g., AD) as described in more detail below.

Accordingly, in some embodiments, the present invention provides immunoglobulins that bind to the peptides that are at least 80%, 90%, or 100% identical to the peptides encoded by SEQ ID NOs:1-5. In some embodiments, the peptides are from 5 to 20 amino acids in length and the peptides that are at least 80%, 90%, or 100% identical to the peptides encoded by SEQ ID NOs:1-5 provide at least a portion of an epitope within the larger peptide sequence. As used herein, an "antibody or polyclonal antibody" means a protein that is produced in response to immunization with an antigen or receptor. The term "monoclonal antibody" means an immunoglobulin derived from a single clone of cells. All monoclonal antibodies derived from the clone are chemically and structurally identical, and specific for a single antigenic determinant. The hybridoma cell lines producing the monoclonal antibodies also are within the scope of this invention.

Laboratory methods for producing polyclonal antibodies and monoclonal antibodies, as well as deducing their corresponding nucleic acid sequences, are known in the art, see Harlow and Lane, Antibodies: A Laboratory Manual, Cold Spring Harbor Laboratory, New York (1988) and Sambrook et al. (1989) supra. The monoclonal antibodies of this invention can be biologically produced by introducing a peptide as described above or a fusion protein or larger protein fragment comprising the peptide into an animal, e.g., a mouse or a rabbit. The antibody producing cells in the animal are isolated and fused with myeloma cells or heteromyeloma cells to produce hybrid cells or hybridomas. Accordingly, the hybridoma cells producing the monoclonal antibodies of this invention also are provided.

Thus, using the peptides described above, and well known methods, one of skill in the art can produce and screen the hybridoma cells and antibodies of this invention for antibodies having the ability to bind to the desired peptide (e.g., SEQ ID NOs:1-5).

If a monoclonal antibody being tested binds with the peptide, then the antibody being tested and the antibodies provided by the hybridomas of this invention are equivalent. It also is possible to determine without undue experimentation, whether an antibody has the same specificity as the monoclonal antibody of this invention by determining whether the antibody being tested prevents a monoclonal antibody of this invention from binding the peptide with which the monoclonal antibody is normally reactive. If the antibody being tested competes with the monoclonal antibody of the invention as shown by a decrease in binding by the monoclonal antibody of this invention, then it is likely that the two antibodies bind to the same or a closely related epitope. Alternatively, one can pre-incubate the monoclonal antibody of this invention with the peptide with which it is normally reactive, and determine if the monoclonal antibody being tested is inhibited in its ability to bind the antigen. If the monoclonal antibody being tested is inhibited then, in all likelihood, it has the same, or a closely related, epitopic specificity as the monoclonal antibody of this invention.

The term antibody also is intended to include antibodies of a different isotype than the monoclonal antibody of this invention. Particular isotypes of a monoclonal antibody can be prepared either directly by selecting from the initial fusion, or prepared secondarily, from a parental hybridoma secreting a monoclonal antibody of different isotype by using the sib selection technique to isolate class switch variants using the procedure described in Steplewski et al. (1985) Proc. Natl. Acad. Sci. 82:8653 or Spira et al. (1984) J. Immunol. Methods 74:307. Thus, the monoclonal antibodies of this invention would include class-switch variants having specificity the desired peptide (e.g., SEQ ID NOs: 1-5).

This invention also provides biological active fragments of the polyclonal and monoclonal antibodies described above. These antibody fragments retain some ability to selectively bind with its antigen or immunogen. Such antibody fragments can include, but are not limited to: (1) Fab, the fragment which contains a monovalent antigen-binding fragment of an antibody molecule produced by digestion with the enzyme papain to yield an intact light chain and a portion of one heavy chain; (2) Fab', the fragment of an antibody molecule obtained by treating with pepsin, followed by reduction, to yield an intact light chain and a portion of the heavy chain; two Fab' fragments are obtained per antibody molecule; (3) (Fab')$_2$, the fragment of the antibody that is obtained by treating with the enzyme pepsin without subsequent reduction; F(ab')$_2$ is a dimer of two Fab' fragments held together by two disulfide bonds; (4) Fv, defined as a genetically engineered fragment containing the variable region of the light chain and the variable region of the heavy chain expressed as two chains; and (5) SCA, defined as a genetically engineered molecule containing the variable region of the light chain, the variable region of the heavy chain, linked by a suitable polypeptide linker as a genetically fused single chain molecule.

Specific examples of "biologically active antibody fragment" include the CDR regions of the antibodies. Methods of making these fragments are known in the art, see for example, Harlow and Lane, (1988) supra.

The antibodies of this invention also can be modified to create chimeric antibodies (Oi, et al. (1986) BioTechniques 4(3):214). Chimeric antibodies are those in which the various domains of the antibodies' heavy and light chains are coded for by DNA from more than one species.

The antibodies of this invention can be linked to a detectable agent or a hapten. The complex is useful to detect the peptides in a sample using standard immunochemical techniques such as immunohistochemistry as described by Harlow and Lane (1988) supra and by the methods describes in more detail below. Examples of types of immunoassays which can utilize monoclonal antibodies of the invention are competitive and non-competitive immunoassays in either a direct or indirect format. Examples of such immunoassays are the enzyme linked immunoassay (ELISA) radioimmunoassay (RIA) and the sandwich (immunometric) and immuno-PCR assays. Detection of the peptide(s) using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

Another technique which may also result in greater sensitivity consists of coupling the antibodies to low molecular weight haptens. These haptens can then be specifically detected by means of a second reaction. For example, it is common to use such haptens as biotin, which reacts avidin, or dinitropherryl, pyridoxal, and fluorescein, which can react with specific anti-hapten antibodies. See Harlow and Lane (1988) supra.

The monoclonal antibodies of the invention can be bound to many different carriers. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art.

In some embodiments, the present invention facilitates the diagnosis, monitoring, and/or determination of risk of developing a disease (e.g., AD) based upon the level of biomarker peptides (e.g., Aβ peptide fragments (e.g., SEQ ID NOs:1-5) in cells (e.g., macrophages, activated macrophages). In some embodiments, the cells (e.g., macrophages, activated macrophages) are isolated from blood (e.g., peripheral blood) and/or cerebrospinal fluid. In some embodiments, the period of time elapsing between cell (e.g., macrophage, activated macrophage) isolation and testing is less than 5 days, less than 4 days, less than 3 days, less than 2 days, less than 1 day, less than 18 hours, less than 12 hours, less than 8 hours, preferably less than 6 hours, and most preferably less than 4 hours. In some embodiments, one or more subcellular fractions are isolated from a cell type (e.g., macrophage, activated macrophage) isolated or purified from a sample. In some embodiments, the subcellular fraction is a lysosomal fraction. In some embodiments, methods of the present invention are combined with ex vivo assessment of phagocytosis activity (e.g., as described in Example 1 and in PCT App. No. PCT/EP09/001210, herein incorporated by reference in its entirety). In some embodiments, such assessment of phagocytosis activity comprises incubation of cells (e.g., macrophages, activated macrophages) from a sample with or without peptides (e.g., Aβ peptide fragments (e.g., SEQ ID NOs:1-5). In some embodiments, phagocytosis is assessed using techniques such as fluorescence-activated cell sorting (FACS) and/or confocal microscopy. In some embodiments, methods of the present invention include the use of techniques such as immunoprecipitation alone or in combination with mass spectrometry (e.g., IP-MS). In some embodiments, methods of the present invention comprise use of antibodies specific to Aβ peptide fragments (e.g., SEQ ID NOs:1-5). In some embodiments, methods of the present invention find use in monitoring treatment efficacy and/or disease progress. In some embodiment, methods of the present invention find use in diagnosing, monitoring, and/or assessing the risk of developing diseases involving monocyte/macrophage activation, extravasation, phagocytosis and re-entry to the circulation. In some embodiments, methods of the present invention find use in monitoring the phagocytosis of amelyoid precursor protein (APP). While the present invention is not limited to any particular mechanism, and an understanding of the mechanism is not necessary to practice the present invention, it is contemplated that APP phagocytosis is a central mechanism in brain APP-amyloid homeostasis altered during the progression of Alzheimer' disease.

An embodiment of the present invention will now be described. A sample of cerebrospinal fluid (CSF) is obtained from a patient by lumbar puncture. The macrophages in the sample are stained with fluorescent-labeled anti-CD 14 and anti-CD 16 antibodies and the macrophages are then withdrawn from the sample by fluorescence activated cell sorting.

The cells are selected on the basis of CD 14 and CD 16 expression because this enables activated macrophages to be differentiated from quiescent cells (increasing CD 16 expression signifies an activated status). This technique also avoids the inadvertent sampling of other cell types such as CD68 positive dendritic cells. This approach contrasts with that reported by Fiala et al (39) in which CD68 positive cells were selected.

The resultant macrophage cells are lysed and prepared for protein analysis. The cell lysate is mixed with monoclonal antibodies capable of binding fragments of the Aβ protein (SEQ. ID NO.:6, DAEFRHDSGYEVHHQKLVFFAEDVG-SNKGAIIGL MVGGVVIA). Exemplary antibodies are 6E10, 4G8 and 11A50-B10 from Signet Laboratories, Inc., and the antibodies specific for example, SEQ ID Nos:1-5 described above. The 6E10 antibody is used to immunoprecipitate Aβ fragments 1-16, the 4G8 antibody immunoprecipitates Aβ fragments 17-24 and the 1 1A50-B10 antibody immunoprecipitates Aβ fragments 1-40. In alternative embodiments, a different panel of antibodies, specific for other fragments, may be used. The monoclonal antibodies are also coupled to magnetic beads, for example, with beads bound to anti-IgG antibodies. The magnetic beads are used to extract the fragments of the Aβ protein. The antibodies and beads are subsequently removed from the peptide fragments. The peptide fragments are then analyzed by MALDI-TOF mass spectrometry and the sequence of the fragments derived from the molecular mass of each fragment. The results are displayed quantitatively to indicate the relative quantity of each fragment. Where no Aβ protein or Aβ protein fragments are detected in the macrophages, this is indicative that the patient has AD.

The Aβ fragments shown in the IP-MS spectra result from intracellular degradation according to the character of the catalytic active site and conditions of action of intracellular protease/peptidases. Such fragments do not necessarily correspond to the sequences of Aβ fragments found extracellularly in CSF. Thus in some embodiments, in order to identify the exact length of each Aβ fragment obtained in the experiment, the peptides are isolated for determination of their respective amino acid sequences.

It is to be appreciated that the method described above detects the presence of the Aβ protein fragments that are present in vivo in the patient. The method does not involve a separate step of exposing the macrophages to the Aβ protein, in vitro, after extraction from the patient.

In some embodiments, the level of the Aβ protein fragments detected is compared with the level detected in a control individual who does not have AD. In such embodiments, a comparison is made between the level and pattern of Aβ protein fragments from the patient and those of the control individual. Where the level of Aβ protein fragments is significantly below that in the control individual then this is indicative of AD in the patient. Similarly, if the type of Aβ protein fragments present in the individual is significantly different from those in the control individual then this is indicative of AD in the patient. In alternative embodiments, a standard level of Aβ protein fragments is generated by detecting the presence of such fragments in the macrophages in CSF in a plurality of control individuals who do not have AD. The level and pattern of Aβ protein fragments from the patient is then compared with the standard level and a statistically significant reduction in level or difference in pattern of the presence of fragments is indicative of AD.

In other embodiments, a single patient is examined annually over a period of time (e.g. 10 years). On each occasion, the levels of Aβ protein fragments in the macrophages in a CSF sample from the patient is studied as described above. A significant change in the level or pattern of Aβ protein fragments each year, in particular a reduction in the level of the Aβ protein fragments year on year, is indicative of the presence of AD.

In certain embodiments, additional AD markers in the patient are also measured, at the same time as the above-described analysis is carried out. Such additional AD markers include abnormal levels of Aβ42, Tau, Phospho-Tau or the Aβ42/Aβ40 ratio in a CSF sample obtained from the patient or in the RNA profile of a blood or CSF sample obtained from the patient. An abnormal level of some or all of these additional AD markers as well as an abnormal level of Aβ protein fragments in the macrophages in the CSF of the patient is indicative of the presence of AD. An exemplary abnormal (i.e. pathological) level of Aβ42 is a CSF concentration of less than 550 pg/ml. The concentration of Tau is age-dependent, high levels being pathological. A pathological level of Phospho-Tau is a CSF concentration of greater than 85 pg/ml. A pathological level of the Aβ42/Aβ40 ratio is where (Aβ42/Aβ40)×10 is less than 1.

In the above described embodiments, a CSF sample from the patient is obtained.

However, in alternative embodiments, a different type of sample is studied, for example, a blood sample. Such an alternative sample may be used because macrophages circulate from the bone marrow to the CNS and therefore macrophages in the blood of a patient may have been exposed to proteins in the CNS. It is, of course, easier to obtain a blood sample than a CSF sample from a patient.

One embodiment of the present invention uses the following criteria as the basis of a diagnostic test to assess Alzheimer's disease in a patient's activated macrophages/microglia: 1) Fulfillment of disease criteria, 2) Presence and sorting of CD16+ population of cells in CSF and blood with flow cytometry, 3) Presence/absence of Aβ peptide fragments in MS spectra after immunoprecipitation with antibodies, 4) Tailored methods at clinics. Flow cytometry and IP-MS can be replaced by other methods for sorting or distinguishing of cell subtypes and peptide fragment analysis.

Methods of evaluating fulfillment of disease criteria. The patient undergoes a thorough clinical investigation, including a study of medical history, physical, neurological and psychiatric examination, screening laboratory tests and MRI and PET imaging of the brain. The diagnosis of AD is made according to recently published criteria [12]. The patient undergoes a thorough physical and psychological examination when enrolled in the diagnosis program at a hospital. The examination includes neuropsychological questionnaires for identification of cognitive deficits, neurological examination, genetic analysis, CSF biomarkers, imaging and metabolic profile.

Methods of evaluating presence and sorting of CD 16+ population of cells in CSF and blood with flow cytometry. Cells are acquired on a FACSAria Cell-Sorting System and analyzed using FACSDiva software (both Becton Dickinson). CSF cell populations are sorted based on their expression of relevant surface markers (CDs). Cells are gated according to forward- and side light-scattering properties and are positively selected for the presence of CD45+ CD3+ CD4+ CD8 (characterization of T-cell population), and CD45+ CD14+ CD16+ CD 19 (characterization of activated macrophages and B-cell population). In order to preserve the immune cells intact, the cell sorting is performed at a maximum of four hours post puncture. $CD14^+/CD16^+$ sorted cells are lysed and kept frozen at −80° C. for further analysis (protein-analysis). In addition to collecting cells for protein analyses, the flow cytometry results indicate the CSF and periphery (blood) immune cell distribution for the patient.

Method of preparation of cells for immunoprecipitation. CSF cell populations are sorted based on their expression of relevant surface markers (CDs). Cells are gated according to forward- and side light-scattering properties and are positively selected for the presence of CD45+ CD3+ CD4+ CD8 (characterization of T-cell population), and CD45+ CD 14+ CD 16+ CD 19 (characterization of activated macrophages and B-cell population). Cell population and number of cells within each population are obtained and registered. The number of activated cells in 7-10 days post stroke patients is high, suggesting circulation of recruited cells also to the CSF compartment of a large number of immune cells. The number of activated macrophages in AD largely equals that in the MCI/non-AD group. The total of %-activated cells in MS is lower that AD; which may be because the immune process in MS mainly involves T-cells. The sorted cells are washed with 400 μl PBS and centrifuged (4° C., 750×g, 5 min). The supernatant is removed and prepared for IP-MS analysis by adding 10 μL RIPA-buffer for cell lysis and keeping frozen at −80° C. prior to protein-analysis.

Method of immunoprecipitation. An aliquot (4 μg) of the monoclonal antibodies 6E10 (1 mg/mL, epitope 4-9), 4G8 (1 mg/mL, epitope 18-22), or 11A50-B10 (0.5 mg/mL, reactive to the C-terminus) (Signet Laboratories, Inc.) is separately added to 50 μL magnetic Dynabeads (Sheep anti mouse, IgG) and incubated overnight on a rocking platform at +4° C. The remaining unbound antibody is removed by washing twice with phosphate-buffered saline (PBS, pH 7.4). After adding 1 mL CSF to the antibody-coated beads, the incubation is continued for an additional 1 h at +4° C. The beads are pelleted for 5 min by using a magnetic particle concentrator (Dynal MPC) and washed twice with PBS (pH 7.4) and twice with 50 mM ammonium bicarbonate (pH 7.3). After the final wash, the extracted Aβ peptides are eluted by adding 20 μL 0.5% formic acid (FA) in water. After vortexing for 2 min in room temperature, the beads are pelleted using the magnetic particle concentrator and the supernatant is collected. The collected supernatant is dried down in a vacuum centrifuge and redissolved in 5 μL 0.1% FA in 20% acetonitrile (ACN). All solvents used are of HPLC quality and all aqueous solutions are made using 18.2 M deionized water obtained from a Millipore purification system.

Methods of evaluating presence/absence of Aβ in MS spectra after immunoprecipitation. IP-MS is used to isolate and determine the Aβ peptide content (Aβ signature) in the $CD14^+/CD16^+$ macrophages sorted by flow cytometry. Proteolytically processed Aβ peptides are difficult to detect using standard proteomic methods possibly because they comprise a heterogeneous set of both N- and C-terminally truncated peptides, some at low quantity. IP-MS analysis has been used previously to obtain an Aβ peptide signature successfully [43] [44]. Briefly, the Aβ peptides are isolated from lysed macrophages using anti Aβ monoclonal antibodies and magnetic Dynabeads. Then a matrix-assisted laser desorption/ionization time of flight mass spectrometry (MALDI-TOF MS) analysis is performed on the immunoprecipitated peptides and the macrophage Aβ signature is calculated. The Absence of Aβ signal in the specimen is interpreted as a positive AD diagnosis.

Alternative Methodologies. In variants of the above-described methodology, the following techniques are used.
1. Instead of using flow cytometry to sort cells, activated macrophages/microglia cells are withdrawn using magnetic extraction, flotation techniques, or other antibody or affinity-based extraction techniques e.g. chromatography, gradient centrifugation. Alternatively the cells are studied using immunohistochemistry
2. Immunoprecipitation using other antibodies specific for the peptide/protein of interest.
3. Instead of using mass spectrometry, another technique for quantitative or semiquantitative peptide/protein analysis is employed such as: HPLC-fluorescence or -UV, luminescence, streptavidin/biotin systems, immunohistochemistry.

Alternative Conditions. In alternative embodiments a different pathological condition characterized by the presence of fragments of a marker protein in the brains of patients is studied. In each case it is necessary to identify the condition to be studied and the corresponding protein that characterizes the condition. Exemplary conditions include: Parkinson's Disease in which ubiquitin is the characterizing protein; Multiple Sclerosis where myelin basic protein characterizes the condition; FrontoTemporal Dementia and Amyotrophic Lateral Sclerosis which are characterized by the tau protein; and Parkinson's Disease, Lewy body dementia and AD which are characterized by the alpha-synuclein protein. In each case, the method of detection or monitoring is carried out as is described above in relation to AD except that the antibodies used to immunoprecipitate the peptides from the macrophages are substituted with antibodies that are capable of binding fragments of the characterizing protein of the condition. Furthermore, in the case of Multiple Sclerosis, abnormally high levels of the ubiquitin marker protein are indicative of the presence of the condition.

In some embodiments, multiple such conditions are tested for simultaneously by immunoprecipitating cell lysates with multiple sets of antibodies, each set of antibodies being specific for fragments of different characterizing proteins.

In some embodiments of the invention, a diagnostic kit is provided in order to enable the detection of a pathological condition of the invention (that is to say a condition characterized by the presence of fragments of a marker protein in the brain of a patient suffering from the condition). The kit is suitable for use in ordinary clinical laboratories since it is based on an ELISA/immuno-PCR technique and so does not require the use of MALDI-TOF or IP-MS techniques as described in some previous embodiments. The kit comprises a panel of target specific antibodies which are specific for a first epitope of the marker protein. Thus, for example, where the pathological condition to be detected is Alzheimer's disease, the marker protein is the Abeta 42 protein. The kit also comprises a supply of magnetic beads which display macrophage specific antibodies (for example, antibodies specific for the CD 14 and CD 16 cell markers); a cell lysing agent such as RadioImmuno Precipitation Assay (RIPA) Buffer containing 25 mM Tris-HCl pH 7.6, 150 mM NaCl, 1% NP-40, 1% Sodium deoxycholate and 0.1% SDS (Pierce Biotechnology); and a secondary antibody which is specific for a second epitope of the marker protein. The secondary antibody is conjugated to a double-stranded DNA marker molecule.

The kit will now be described in use. A sample, such as a peripheral blood or CSF sample, is obtained from a patient and macrophage cells are isolated from the sample by mixing with the magnetic beads provided in the kit. The macrophage specific antibodies displayed by the magnetic beads bind the macrophages in the patient sample and the macrophages and the magnetic beads are then removed from the sample by magnetic means. The macrophage cells are then released from the macrophage specific antibodies by adjusting the pH of the solution and the macrophage cells are lysed with the lysing agent in order to release the cell contents which includes the marker protein. Also provided in the diagnostic kit is a solid support on which are immobilized a plurality of target antibodies which are specific for the marker protein. The contents of the lysed macrophage cell are then contacted with the solid support such that the first epitope of the marker protein binds to the target antibody.

The solid support is contacted with a secondary antibody which is conjugated to a double-stranded DNA marker molecule. The secondary antibody is specific for the second epitope of the marker protein such that the secondary antibody is immobilized on the solid support where the marker protein is present. Unbound proteins and unbound secondary antibody are then washed out and removed.

The washed solid support is then subjected to real time PCR which melts the double stranded DNA marker molecule and amplifies the copy number in order to identify the number of copies of the DNA marker molecule. The number of copies of the DNA marker molecule after a predetermined number of cycles of PCR amplification is indicative of the starting number of DNA molecules. Furthermore, there is a one-to-one relationship between the starting number of DNA molecules and the number of bound marker proteins. Therefore, this immuno-PCR technique provides an accurate indication of the number of marker protein molecules in the patient sample.

Accordingly, such diagnostic kits allow a simple immunological method to be used in standard clinical laboratories which are available in all hospitals, private clinics and commercial laboratories in order to analyze patient samples in accordance with the present invention. The use of the kit of the invention does not require the use of expensive or advance laboratory instruments and detection using an immuno-PCR technique ensures high sensitivity.

In some variants of the above-described diagnostic kits, a plurality of panels of antibodies are provided in the kit. For example, in one variant, the kit comprises first target antibodies that are specific for a first epitope (e.g., SEQ ID Nos:1-5) of the Aβ protein and second target antibodies which are specific for a second epitope of the Aβ protein (e.g., SEQ ID Nos:1-5). In still further embodiments, a plurality of panels of antibodies are provided in the kit and the antibodies are specific for marker proteins corresponding to more than one pathological condition. For example, in one particular variant, a panel of antibodies is provided which is specific for the Abeta protein (the marker protein for Alzheimer's disease) and a panel of antibodies is provided specific for Multiple Sclerosis (where myelin basic protein is the marker protein). In these variants, it is preferred that different panels of secondary antibodies, each specific for a respective marker protein and each conjugated to a different DNA marker molecule, are provided such that the signal for the detection of each marker protein is distinguishable.

In the above described embodiments of the diagnostic kit, the detectable label is a DNA marker molecule. However, in other embodiments, a different detectable label is used. For example, the detectable label may be a fluorophore, a latex microbead or a gold particle. Such alternative detectable labels are useful when the kit is provided only to provide a qualitative result rather than a quantitative result.

In some alternative embodiments of the kit, a lysing agent, as such, is not provided. Instead, cells are lysed mechanically, e.g. by centrifugation, prior to isolation of the macrophages.

It is also to be appreciated that the diagnostic kits of the present invention are not limited to kits comprising antibodies. In alternative embodiments, the antibodies of the kit are replaced with other binding reagents such as antigen binding fragments (e.g. F(ab')$_2$ fragments or Fab fragments) or a polynucleotide sequence. Typically such other binding reagents have binding affinities for their target comparable to that of antibodies such as having a binding affinity of less than 100 nm in an aqueous buffered solution at between pH 4 and 8.

EXAMPLES

The following examples are provided in order to demonstrate and further illustrate certain preferred embodiments and aspects of the present invention and are not to be construed as limiting the scope thereof.

Example 1

Identification of Amyloid Beta (Aβ) Peptides in Isolated Monocytes/Macrophages

Peripheral blood monocytes/macrophages from a healthy volunteer were isolated and incubated with addition of synthetic Aβ$_{42}$ in the growth medium overnight to facilitate uptake and phagocytosis of Aβ$_{42}$. A control sample without addition of Aβ$_{42}$ was also included. Sample collection and monocyte/macrophage isolation was as described in in PCT App. No. PCT/EP09/001210, herein incorporated by reference in its entirety.

After cells were harvested, cellular organelles (ER, mitochondria, endosomes, lysosomes etc) were extracted and subsequently separated on an Iodixanol gradient by ultracentrifugation. Polypeptides present in the organelle fraction corresponding to the lysosomes were analyzed using mass spectrometric analysis with database searches based upon the Aβ42 amino acid sequence.

Figure 4:
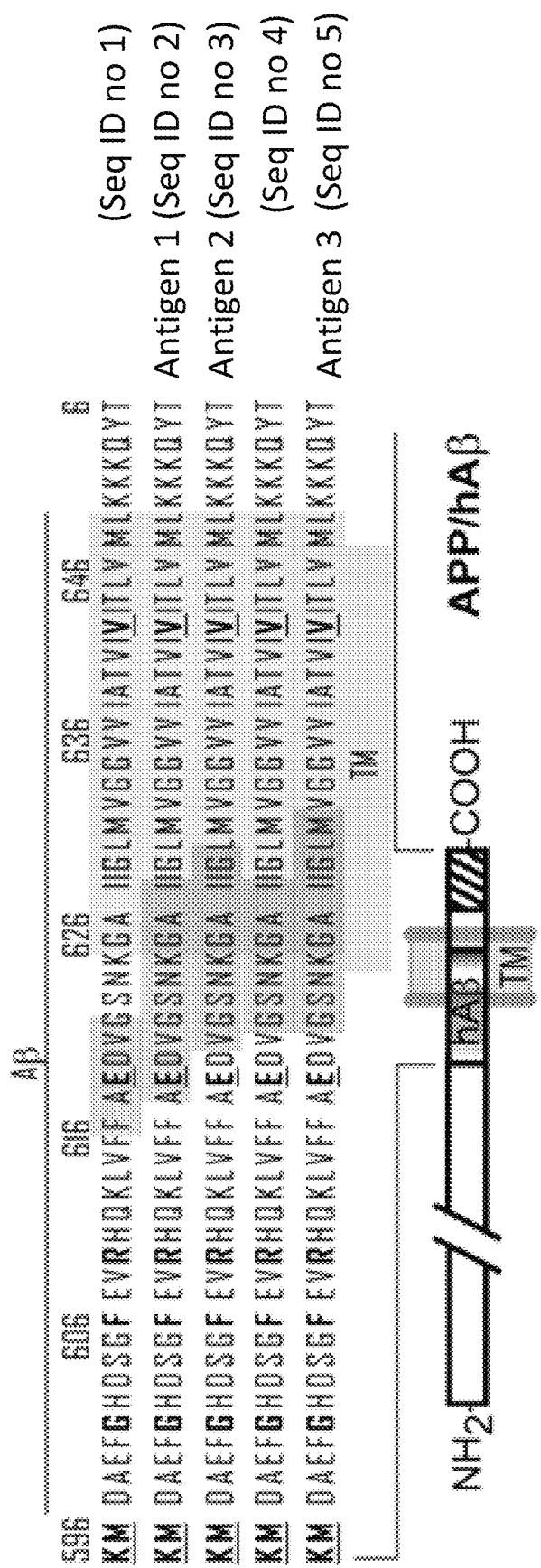
FIG. 4 shows a representation of the Aβ-peptides identified through mass spectrometry (MS)-analysis as described herein. The central shaded fields show the location of the individual peptides within the $A\beta_{1-42}$-molecule. The overlapping shaded region to the right of the central shaded region shows the transmembrane region. All peptides border the intramembrane (transmembrane) region of the molecule.
Figure 5:
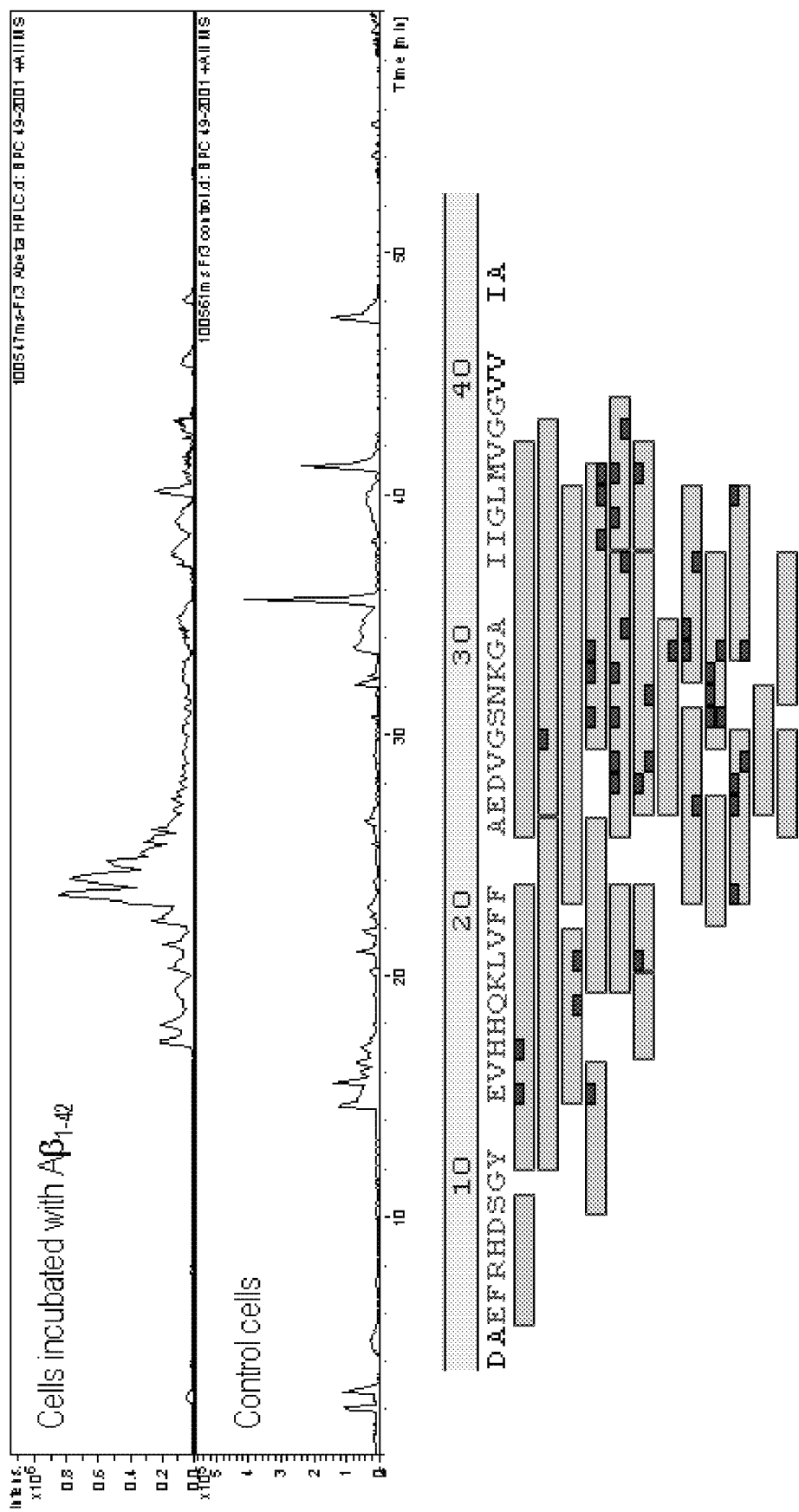
FIG. 5 shows results of mass spectrometry (MS)-analysis during experiments conducted during the course of developing some embodiments of the present invention. The upper panel shows the crude MS-spectrum from lysosomes of cells incubated in the presence of $A\beta_{1-42}$ and from control cells. The lower panel shows further analysis of MS-data from the upper panel based on the $A\beta_{1-42}$ sequence; grey bars indicate potential fragments and dark shaded squares indicate significant hits within these fragments.

Several Aβ$_{42}$ fragments were identified and found to be specific for the Aβ$_{42}$-phagocytosis condition. In addition, two shorter peptides were unequivocally identified and still sufficiently long to highly likely present antigenic epitopes, the stretches GSNKGAI (25-32 of the Aβ42 molecule, corresponding to the sequence 621-627 of the APP, and FAEDVG (20-25 of the Aβ42 molecule, corresponding to 616-621 in APP) both partially in the transmembrane region (FIG. 4).

Five new Aβ$_{1-42}$ fragments were identified and these highly likely present antigenic epitopes. These fragments are depicted as SEQ ID NOs: 1-5 in FIG. 2 and have the following amino acid sequences:

```
SEQ ID NO: 1:
FAEDVG
(20-25 of the Aβ₁₋₄₂molecule, corresponding to
616-621 in APP)

SEQ ID NO: 2:
AEDVGSNKGAI
(21-31 of the Aβ₁₋₄₂molecule, corresponding to
the sequence 617-627 of the APP)

SEQ ID NO: 3:
GSNKGAIIGLM
(25-35 of the Aβ₁₋₄₂molecule, corresponding to
621-631 in APP)

SEQ ID NO: 4:
GSNKGAI
(25-32 of the Aβ₁₋₄₂molecule, corresponding to
the sequence 621-627 in APP)

SEQ ID NO: 5:
VGSNKGAIGL
(24-34 of the Aβ₁₋₄₂molecule, corresponding to
the stretch 620-630 in APP)
```

All fragments are located within the intramembrane region of the Aβ$_{1-42}$ molecule. While the present invention is not limited to any particular mechanism, and an understanding of the mechanism is not necessary to practice the present invention, it is contemplated that they are likely to be generated by Aβ-cleaving enzymes such as insulin degrading enzyme (IDE) and neprilysin (Malito et al. (2008) Cell Mol Life Sci, 65:2574-2585; herein incorporated by reference in its entirety Example 2

Synthesis of Antigens

Based on the experiment described in Example 1, the following peptides were selected for further study and produced by Eurogentec, (MedProbe Norway):

```
Antigen 1 (SEQ ID NO: 2):
H₂N-AED VGS NKG AI-CONH₂

Antigen 2 (SEQ ID NO: 3):
H₂N-GSN KGA IIG LM-CONH₂

Antigen 3: (SEQ ID NO: 5):
H₂N-VGS NKG AIG L-CONH₂
```

Example 3

Immunization of Mice in Order to Obtain Response Towards the Synthetic Peptides. Establishment of Clones Producing Monoclonal Antibodies Against Alzheimer-Specific $A\beta_{1-42}$ Metabolites from within the Lysosomes of Monocytes Animals: 6 BALB/c female mice, 10 NMRI mice The BALB/c mice were immunized 27/12-10 with the regime outlined in Table 1. A second immunisation (boost) was performed 31/1-11, the same regime applied without adjuvants and the peptide was injected IP and IV. Blood was drawn from the mice and analysed at Diatec Monoclonals AS for presence of specific antibodies. Macrophages from the NMRI mice served as feeder cells for antibody production in vitro. Screening of blood samples from the mice nr 1-6 against the mix of antigens with or without KLH resulted in positive hits from mouse nr 1, 4 and 5 and negative hits from mouse nr 6. Blood from mouse nr 2 was negative while blood from mouse nr 3 was strongly positive for the peptide mix including KLH, indicating an immune response towards KLH instead of the peptides. Spleens from the three positive mice+ the control mouse in Week 7 2011 were extracted, thus concluding the animal work without a third immunization boost.

TABLE 1

| Mouse nr | Peptide | Adjuvant |
|---|---|---|
| 1 | Ag1 200 µL IP | Freunds adjuvant complete |
| 2 | Ag2 200 µL IP | 200 µL IP |
| 3 | Ag1 66.7 µL IP | (1:1 emulsion with peptide) |
| 4 | Ag2 66.7 µL IP | |
| 5 | Ag3 66.7 µL IP | |
| 6 | PBS 200 µL IP | |

The spleens of mice that included antibodies against the peptides were disintegrated and cells were incubated with feeder cells from NMRI-mice for clonal expansion. After ELISA and a $2^{nd}$ recloning of selected clones showing good specificity against the antigen clone 6D3/1/15 (mouse 5), 2A3/1/13 (mouse 1) and 3B7/1/16 (mouse 5) gave good results. All three clones gave specific response against antigen 1 and were included in a cellbank and master cell bank (MCB). A test production from one (from the MCB) ampoule from each clone are performed. Concentration: 1 mg/mL, 0.09% azide. 3B7/2/6 (6.7 mL), 2A3/2/15 (12.2 mL), 6D3/2/22 (28 mL). Delivered 29.06.2011. Isotype Mouse IgG.

Example 4

Measurement of Antigen Presence in Biological Sample Using THP-1-Acute Monocytic Leukemia Cells (American Type Culture Collection (ATCC)

Figure 6:
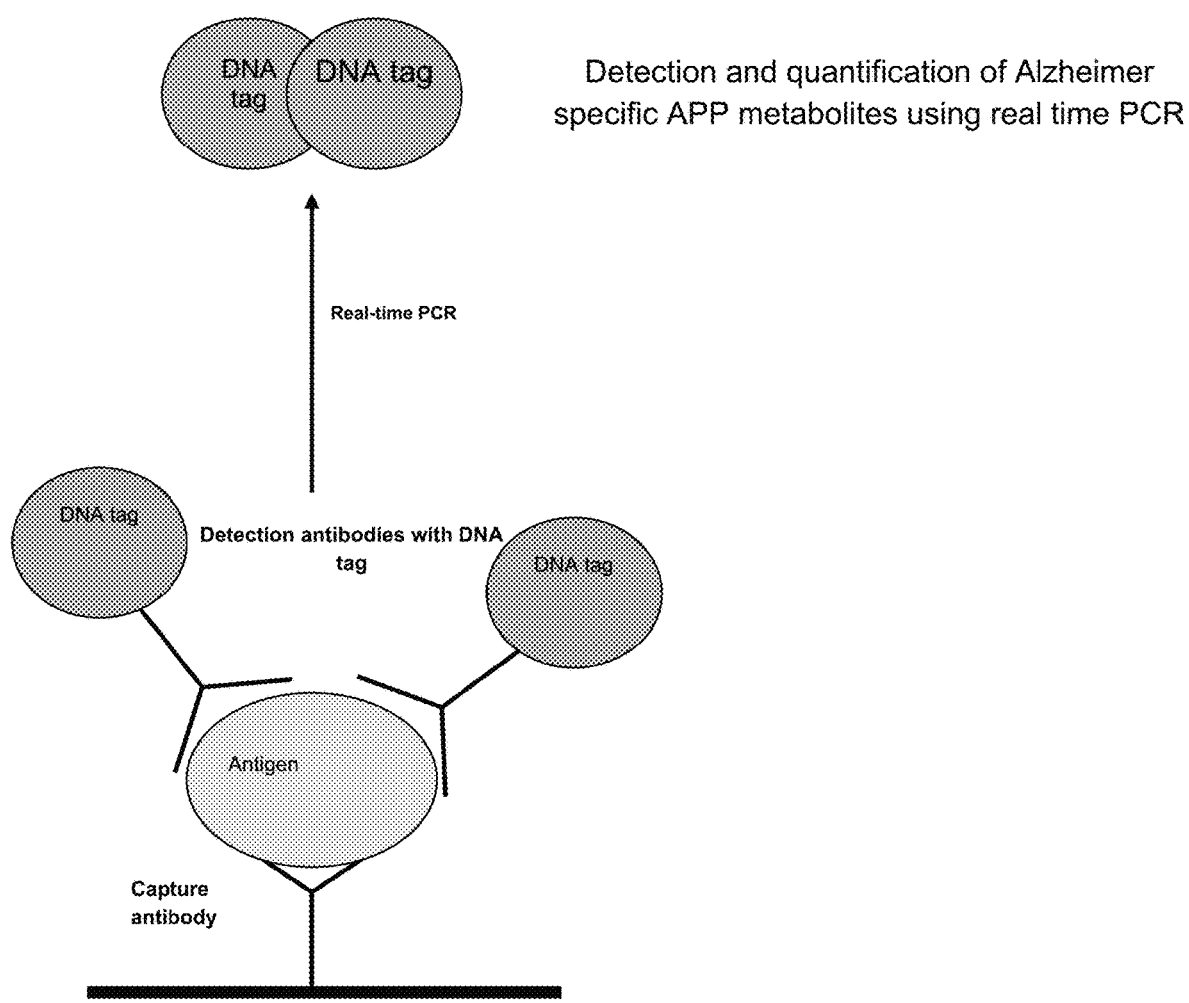
FIG. 6 provides a schematic depiction of an assay for detection and quantification of Alzheimer specific APP metabolites using real time PCR.

FIG. 6 provides a schematic depiction of an Immune-PCR assay using the antibodies described in Example 3. The capture antibody is one of the three antibodies developed via immunization. The two other antibodies will be directly conjugated with a specific DNA tag that is amplified using real-time PCR.

For the assay, THP-1 cells are cultivated in 2 bottles with RPMI medium containing 10% FBS and 1% antibiotic. The cells are differentiated using a final concentration of 100 nM TPA for 17 h. To one bottle is added synthetic $A\beta_{1-42}$ to a final concentration of 2.5 ng/µL, the other kept untreated. The cells are incubated over night at 37° C. in a humidified atmosphere with 5% $CO_2$. The cells are then washed and trypsinated (Trypsin-Versene (EDTA) from Lonza) in order to release the attached cells from the bottom surface.

Flowcytometry of THP-1 Cells.

The cells are counted and four tubes containing 100 000 cells each are subjected to fixation and permeabilization using the IntraPrep kit from Beckman Coulter, Inc, USA to allow for staining of intracellular targets. Two tubes (one tube that has received Aβ and one untreated) are stained with two commercially available monoclonal antibodies against $A\beta_{1-42}$ (6E10 and 4G8 originating from mice) and two tubes (one tube that has received Aβ and one untreated) are stained with appropriate isotype control antibodies (Mouse IgG1 and IgG2b). All these antibodies are obtained from Nordic BioSite AS, Norway. The secondary antibody AlexaFluor488-Goat anti-Mouse (Invitrogen Dynal AS, Norway) is used to detect both the Aβ-specific antibodies and the isotype controls. The cells are kept in IOTest3 Fixative solution (Beckman Coulter, INC, USA) at 4° C. over night before flow cytometric analysis on a FACS Cantoll from BD. The cells are finally acquired and gated based on scatter and fluorescent properties. Monocytes/macrophages positive for AlexaFluor488, i.e. with higher fluorescent signal than isotype controls, are considered Aβ-positive. Analysis is performed using FACS Diva software (BD).

Preparation of Samples for Immuno-PCR.

The remaining cells (approx. 319 000 cells receiving $A\beta_{1-42}$ and approx. 560 000 cells untreated) are centrifuged at 1000 g for 10 min. The supernatant are removed and 404 lysing agent, M-PER® (Mammalian protein extraction reagent from Pierce)) added 1% protease inhibitor cocktail (Sigma Life Sciences) are added to the cell pellet.

The lysates are incubated in a mixer for 30 minutes at room temperature. After incubation the samples are kept frozen until analysis.

The detection antibody 3B7/2/6 is biotinylated in house (Lightning-Link Biotin Conjugation Kit Type A (Innova Biosciences)) in order to bind to anti-biotin detection conjugate.

The development of immuno-PCR is performed using the Imperacer® assay development kit (Chimera Biotec, Germany).

Assay pre-preparation—Immobilization of capture antibody. Antibody 6D3/2/22 is diluted in coating buffer (final concentration 10 µg/ml). 30 µL of diluted antibody are added into each well. The wells are sealed with foil and incubated for at least 16 hours at 4° C. The wells are washed and chimera direct block (240 µL/well) is added for 30-60 seconds at room temperature with orbital shaking. 30 µL of four dilutions using the synthesized antigen 1 are added to each well (0 ng/mL, 0.1 ng/mL, 1 ng/mL, and 10 ng/mL) as standards. 30 µL of lysate from Aβ treated and untreated cells is added to each well. The samples are incubated for 30 minutes at room temperature during orbital shaking.

After incubation of the analyte, 30 µL of biotinylated primary detection antibody (antibody 3B7/2/6, final concentration 1 µg/ml) is added to the sample in order to be coupled to the immobilized analyte. The samples are incubated for 30 minutes at room temperature and orbital shaking.

After incubation with primary detection antibody, 30 µL/well of diluted Imperacer® Conjugate CHI-Biotin (1:3000) is added to the samples. The samples are incubated for 30 minutes at room temperature with orbital shaking.

The samples are washed and 35 µL of PCR mastermix is added. The wells are then incubated at 95° C. for 5 minutes. After incubation 30 µl of the samples are transferred to the reaction plate (Micro Amp Fast Optical 96-well Reaction Plate (Applied Biosystems)). In addition to standards and samples a positive and negative PCR control are included in the reaction plate.

Real-Time PCR.

The PCR is carried out using 7900HT Fast Real-Time PCR system (Applied Biosystems). FAM is set up as a fluorophor (emission at 518 nm).

TABLE 2

Real-time PCR program:

| Time | Temperature | Repeats |
|---|---|---|
| 4 minutes | 95° C. | 1x |
| 12 seconds | 95° C. | 50x |
| 30 seconds | 50° C. | |
| 30 seconds | 72° C. | |

Figure 7:
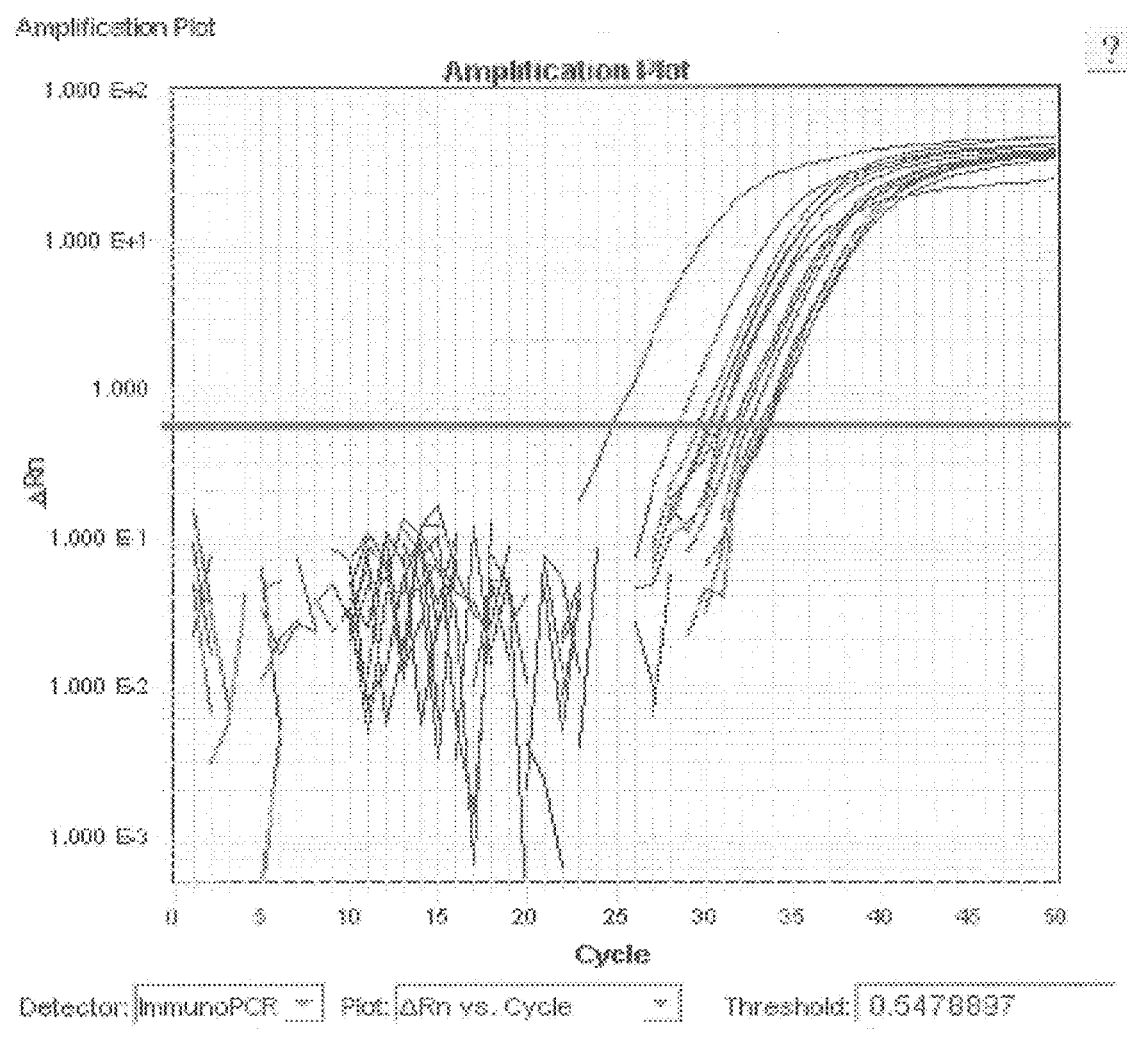
FIG. 7 provides an amplification plot from real-time PCR
Figure 8A:
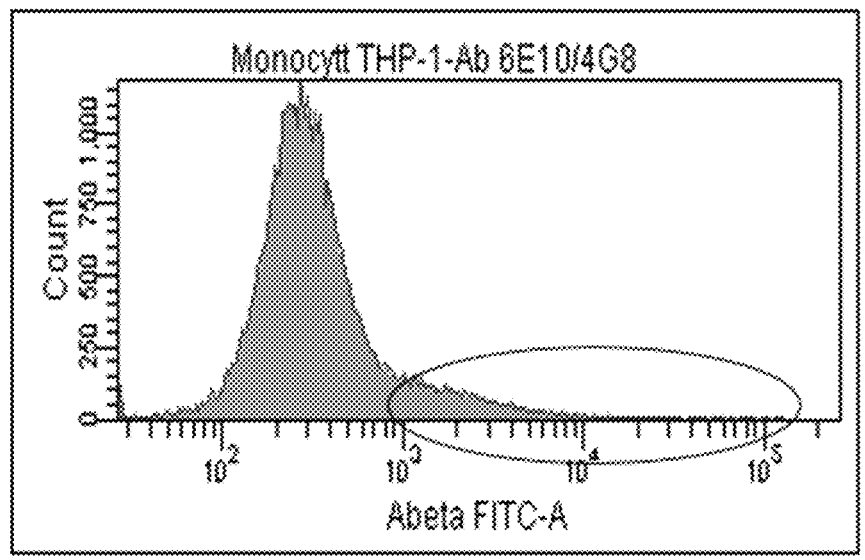
FIG. 8A and FIG. 8B provide histograms for THP-1 cells after flowcytometry. Histogram 8a shows THP-1 cells added $A\beta_{1-42}$ in medium. Histogram 8b shows THP-1 cells without $A\beta_{1-42}$ in medium. The intracellular Aβ content is illustrated in the histograms. Isotype median Abeta FITC-A signal is 102 (Results not shown). A shift in Abeta FITC-A to the right compared to the isotype is indicating cells with presence of intracellular Aβ. The ellipse in histogram 8a shows presence of a tail of Aβ positive cells that is absent in histogram 8b. This tail is indicating a higher amount of cells containing phagocytosed intracellular Aβ in histogram 8b.
Figure 8B:
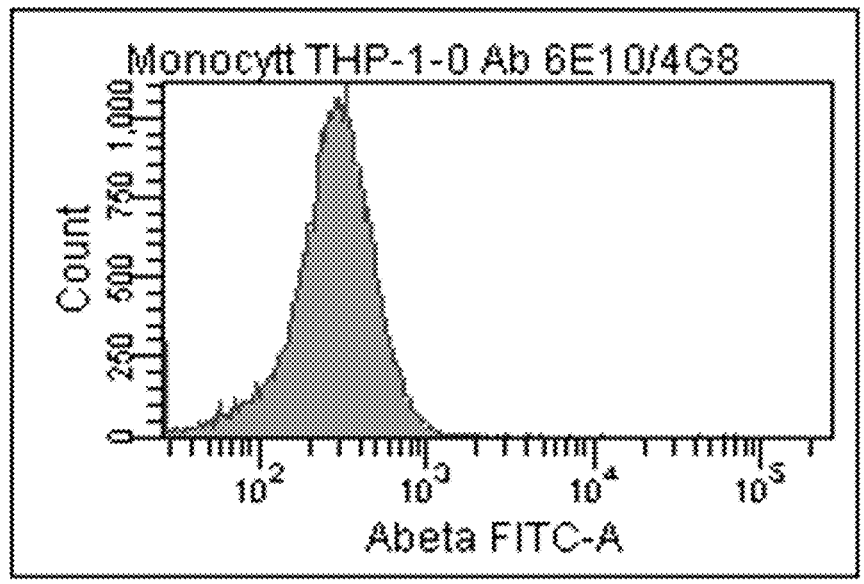
Figure 9:
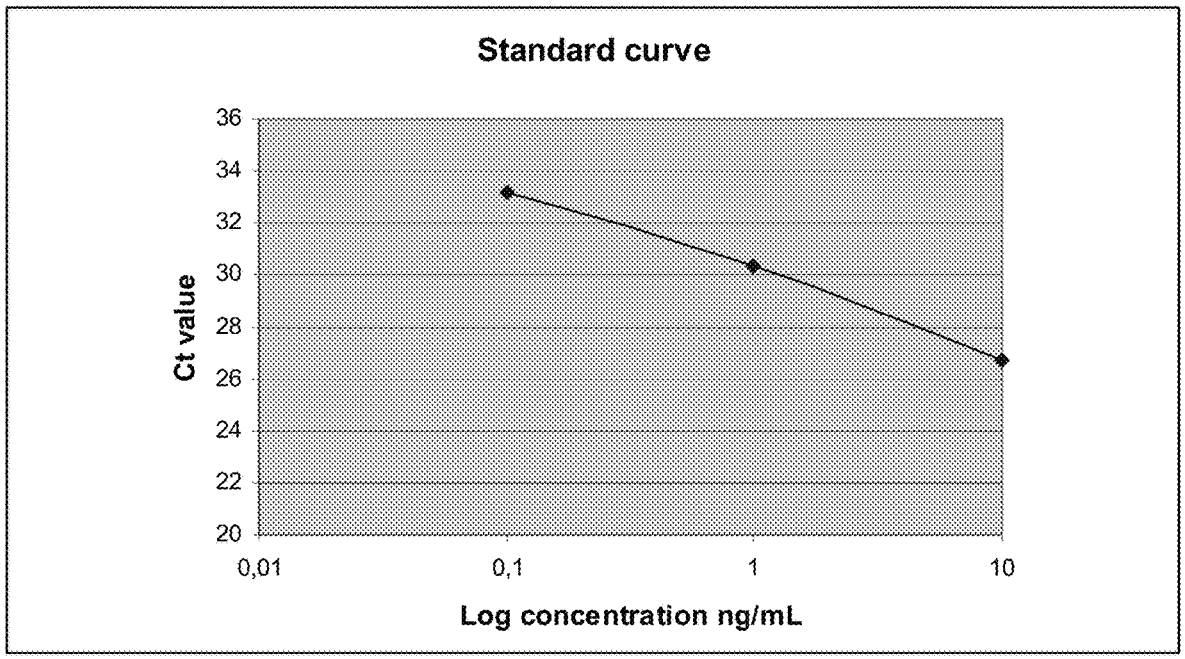
FIG. 9 provides a standard PCR curve showing threshold cycle (Ct value) vs. log peptide concentration. The graph shows the threshold cycle (Ct value) against log concentration. Equation for the curve is y=−0.6056x+32,629. $R^2$=0.8653.

The results are provided in FIG. 7, FIG. 8 and Table 3.

TABLE 3

| Sample | Ct-value |
|---|---|
| 0 ng/mL | 33.497 |
| 0.1 ng/mL | 33.216 |
| 1 ng/mL | 30.347 |
| 10 ng/mL | 26.734 |
| Cell lysate from THP-1 cells receiving Aβ | 29.65 |
| Cell lysate from THP-1 untreated | 30.332 |

The Ct value represents the first PCR cycle at which the reporter signal exceeds the signal of a given uniform "Threshold".

Conclusion.

The Ct value for the sample receiving additional Aβ is lower than the untreated sample. The concentration for this sample is 4, 91 ng/mL when using the equation for the standard curve. The concentration for the untreated sample is 3, 79 ng/mL. This indicates a higher presence of antigen 1 in cell lysate receiving Aβ and shows that it is possible to measure degradation products of Aβ in biological samples with this method.

Example 5

Measurement of Antigen Presence in Monocytes/Macrophages from Patient with AD (F, Age 62) and Healthy Control (Spouse)(M, Age 60)

Heparinized blood (8 ml) is drawn by venipuncture. From the blood sample, peripheral blood mononuclear cells (PBMC's) are isolated with Histopaque®1077 from Sigma-Aldrich Corporation, USA, i.e. the granulocytes and the red blood cells are excluded from the following steps. The monocytes/macrophages are isolated from the other cells using flow cytometry. The cells are analyzed on a FACS Aria from BD. The cells are acquired and gated based on forward scatter (size) and side scatter (granularity) properties. The monocyte/macrophage population is sorted into dedicated tubes (Patient and Control).

Flowcytometry of Monocytes/Macrophages from Patient and Control

Intracellular staining of macrophages/monocytes from patient and control using commercially available monoclonal antibodies against $A\beta_{1-42}$. All cells subjected to fixation and permeabilization using the IntraPrep kit from Beckman Coulter, Inc, USA to allow for staining of intracellular targets. One tube (100 000 PBMC) from both patient and control is stained with two commercially available monoclonal antibodies against Aβ42 (6E10 and 4G8 originating from mice) and one tube from both patient and control are stained with appropriate isotype control antibodies (Mouse IgG1 and IgG2b). All these antibodies are obtained from Nordic BioSite AS, Norway. The secondary antibody AlexaFluor488-Goat anti-Mouse (Invitrogen Dynal AS, Norway) is used to detect both the Aβ-specific antibodies and the isotype controls. The cells are kept in IOTest3 Fixative solution (Beckman Coulter, INC, USA) at 4° C. for up to 5 days before flow cytometric analysis on a FACS Cantoll from BD. Monocytes/macrophages positive for AlexaFluor488, i.e. with higher fluorescent signal than isotype controls, are considered Aβ-positive. Analysis is performed using FACS Diva software (BD).

Preparation of Cells for Immuno-PCR

Monocytes/macrophages (440 000 cells) are centrifuged at 1200 g for 10 min. The supernatant are removed and 50 µL lysing agent, M-PER® (Mammalian protein extraction reagent from Pierce) added 1% protease inhibitor cocktail (Sigma Life Sciences) are added to the cell pellet.

The lysates are incubated in a mixer for 30 minutes at room temperature. After incubation the samples are kept frozen until analysis.

Immuno-PCR.

Immuno-PCR is conducted as described above. 30 µL of four dilutions using the synthesized antigen 1 are added to each well (0 ng/mL, 0.1 ng/mL, 0.5 ng/mL, and 1.0 ng/mL) as standards.

Results Example 5

Figure 10A:
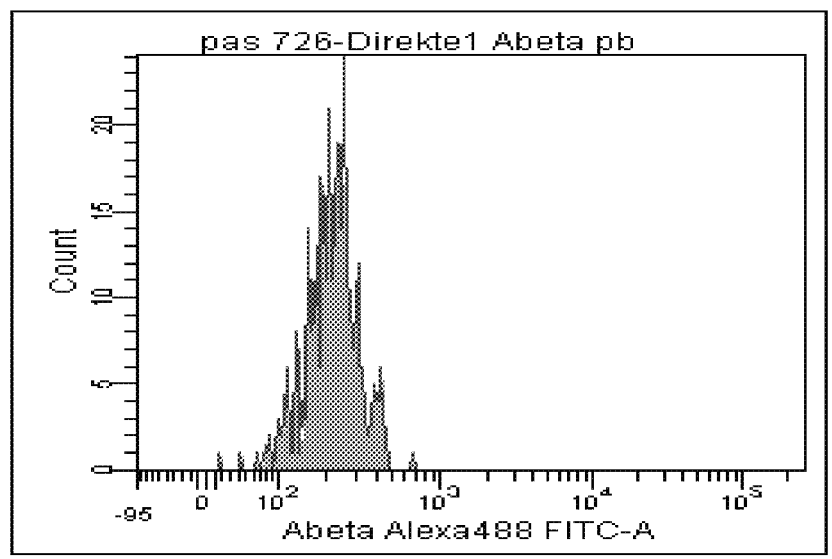
FIG. 10A and FIG. 10B provide histograms for monocytes/macrophages from patient and control after flowcytometry. 10a shows patient sample stained intracellular with 6E10/4G8. 10b shows control sample stained intracellular with 6E10/4G8. The intracellular $A\beta_{1-42}$ content in macrophages/monocytes from patient and control is illustrated in the histograms. Isotype median Abeta FITC-A signal is 102 (Results not shown). A shift in Abeta FITC-A to the right compared to the isotype is indicating cells with presence of intracellular $A\beta_{1-42}$. Histograms 3 and 4 are indicating presence of approx. of intracellular $A\beta_{1-42}$ when compared to the isotypes.
Figure 10B:
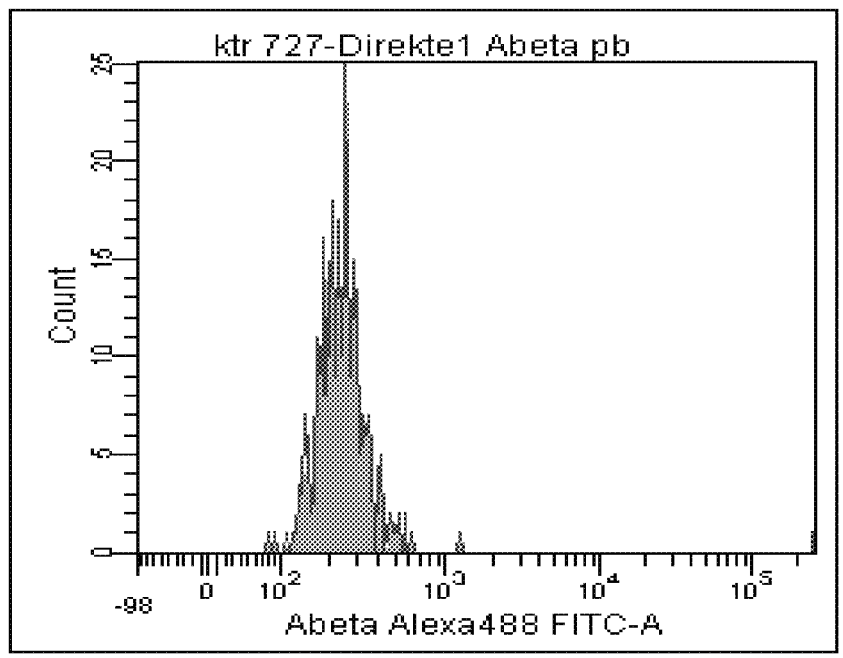

Results from the flowcytometry analysis are provided in FIG. 10 (histograms 10a and 10b).

Real-Time PCR

Figure 11:
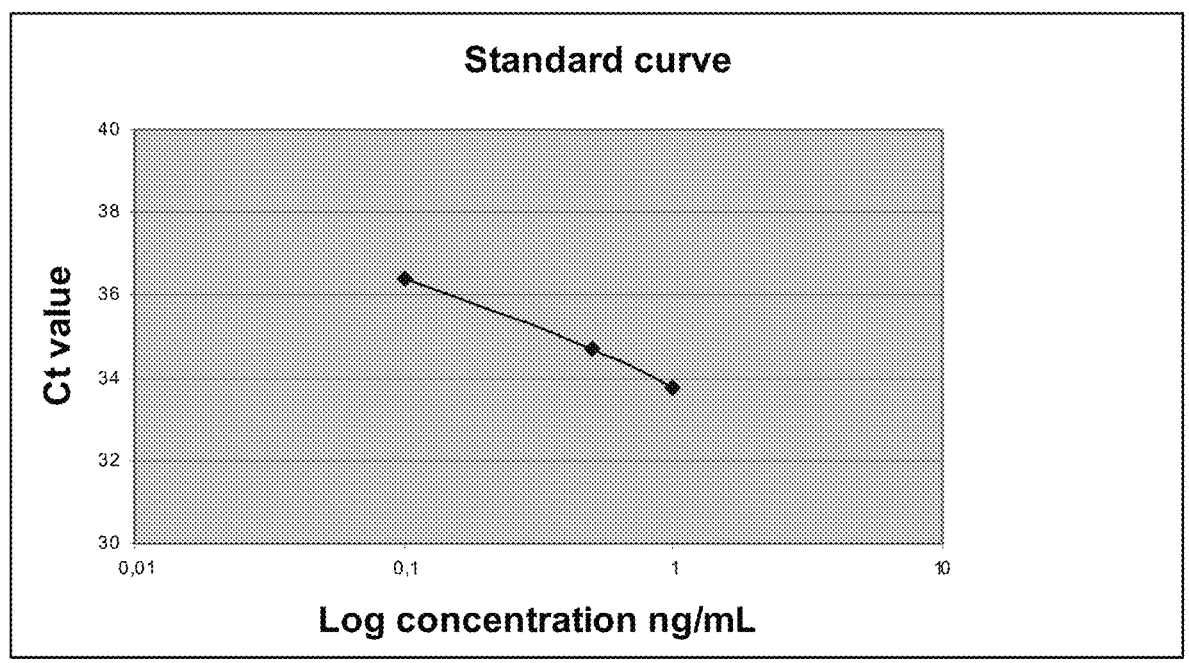
FIG. 11 provides a standard PCR curve showing threshold cycle (Ct value) vs. log peptide concentration. The graph shows the threshold cycle (Ct value) against log concentration. Equation for the curve is y=−3,8956x+37,275. $R^2$=08818.

Results are provided in table 4 and FIG. 11.

TABLE 4

| Sample | Ct-value |
|---|---|
| 0 ng/mL | 38.005 |
| 0.1 ng/mL | 36.419 |
| 0.5 ng/mL | 34.708 |
| 1 ng/mL | 33.736 |
| Patient | 36.415 |
| Control | 35.71 |

The Ct value represents the first PCR cycle at which the reporter signal exceeds the signal of a given uniform "Threshold".

Conclusion:

The Ct value for the control is lower than for the patient. The concentration for the control is 0, 40 ng/mL when using the equation for the standard curve. The concentration for the patient is 0, 22 ng/m, showing a higher amount of antigen 1 in cells from control compared to patient. Although both patient and control seems to have close to equal amount of intracellular A$\beta_{1-42}$ as shown with flowcytometry, this real-time PCR result indicates that this method can be used to measure specific degradation products in biological samples differentiating patient from controls.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in diagnostic assays, the medical arts, or related fields are intended to be within the scope of the following claims.

We claim:

1. A method for detecting peptides in a sample, said method comprising:
   a) obtaining a body fluid sample from a patient; and
   b) detecting the presence of a peptide consisting of an amino acid sequence corresponding to SEQ ID NO:5.

2. The method of claim 1, wherein the body fluid sample comprises a cell type selected from the group consisting of leucocytes, monocytes, peripheral blood macrophages, and activated macrophages from peripheral blood.

3. The method of claim 2, wherein said cell type is a monocyte.

4. The method of claim 3, wherein said monocyte is from peripheral blood.

5. The method of claim 1, wherein said body fluid sample is serum.

6. The method of claim 1, wherein said body fluid sample is plasma.

7. The method of claim 1, wherein said body fluid sample is cerebrospinal fluid.

8. The method of claim 1, wherein said detecting is performed in conjunction with monitoring efficacy of a treatment.

* * * * *

```
                        SEQUENCE LISTING

<160> NUMBER OF SEQ ID NOS: 6

<210> SEQ ID NO 1
<211> LENGTH: 6
<212> TYPE: PRT
<213> ORGANISM: Homo sapiens

<400> SEQUENCE: 1

Phe Ala Glu Asp Val Gly
1               5

<210> SEQ ID NO 2
<211> LENGTH: 11
<212> TYPE: PRT
<213> ORGANISM: Homo sapiens

<400> SEQUENCE: 2

Ala Glu Asp Val Gly Ser Asn Lys Gly Ala Ile
1               5                   10

<210> SEQ ID NO 3
<211> LENGTH: 11
<212> TYPE: PRT
<213> ORGANISM: Homo sapiens

<400> SEQUENCE: 3

Gly Ser Asn Lys Gly Ala Ile Ile Gly Leu Met
1               5                   10

<210> SEQ ID NO 4
<211> LENGTH: 7
<212> TYPE: PRT
<213> ORGANISM: Homo sapiens

<400> SEQUENCE: 4

Gly Ser Asn Lys Gly Ala Ile
1               5

<210> SEQ ID NO 5
<211> LENGTH: 10
<212> TYPE: PRT
<213> ORGANISM: Homo sapiens

<400> SEQUENCE: 5

Val Gly Ser Asn Lys Gly Ala Ile Gly Leu
1               5                   10

<210> SEQ ID NO 6
<211> LENGTH: 42
<212> TYPE: PRT
<213> ORGANISM: Homo sapiens

<400> SEQUENCE: 6

Asp Ala Glu Phe Arg His Asp Ser Gly Tyr Glu Val His His Gln Lys
1               5                   10                  15
```

```
Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```